(12) United States Patent
Onodera et al.

(10) Patent No.: US 9,689,042 B2
(45) Date of Patent: Jun. 27, 2017

(54) USE OF GLYCOLYTIC PATHWAYS FOR INHIBITING OR MEASURING ONCOGENIC SIGNALING

(71) Applicant: The Regents of the University of California, Oakland, CA (US)

(72) Inventors: Yasuhito Onodera, Sapporo (JP); Mina Bissell, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 555 days.

(21) Appl. No.: 14/020,361

(22) Filed: Sep. 6, 2013

(65) Prior Publication Data

US 2014/0073523 A1 Mar. 13, 2014

Related U.S. Application Data

(60) Provisional application No. 61/698,213, filed on Sep. 7, 2012.

(51) Int. Cl.
| | | |
|---|---|---|
| *A61K 36/00* | (2006.01) | |
| *C12Q 1/68* | (2006.01) | |
| *G01N 33/68* | (2006.01) | |
| *G01N 33/574* | (2006.01) | |
| *A61K 39/00* | (2006.01) | |

(52) U.S. Cl.
CPC ..... *C12Q 1/6886* (2013.01); *G01N 33/57415* (2013.01); *G01N 33/6854* (2013.01); *A61K 2039/517* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,695,937 A | 12/1997 | Kinzler et al. | |
| 6,103,734 A | 8/2000 | Legarda Ibanez | |
| 8,132,676 B2 | 3/2012 | Peters et al. | |
| 2010/0279301 A1* | 11/2010 | Chinnaiyan | C12Q 1/6886 435/6.14 |

FOREIGN PATENT DOCUMENTS

| | | |
|---|---|---|
| WO | 99/07870 A1 | 2/1999 |
| WO | 00/71739 A1 | 11/2000 |

OTHER PUBLICATIONS

Zhao, et al., "Functional Properties and Genomics of Glucose Transporters", Current Genomics, 2007, 8, 113-128.
Rossetti, Luciano, "Perspective: Hexosamines and Nutrient Sensing", Endocrinology, vol. 141, No. 6, 2000, pp. 1922-1925.
Enserink, et al., "The cAMP-Epac-Rap1 pathway regulates cell spreading and cell adhesion to laminin-5 through the alpha3beta1 integrin but not the alpha6beta4 integrin", The Journal of Biological Chemistry, vol. 279, No. 43, Oct. 22, 2004, pp. 44889-44896.
Onodera, et al., "Increased sugar uptake promotes oncogenesis via EPAC/RAP1 and O-GlcNAc pathways", The Journal of Clinical Investigation, vol. 124, No. 1, Jan. 2014, pp. 367-384.

* cited by examiner

*Primary Examiner* — Jim Ketter
(74) *Attorney, Agent, or Firm* — Brian E. Davy; Bozicevic, Field & Francis LLP

(57) ABSTRACT

Disclosed are methods in which glucose metabolism is correlated to oncogenesis through certain specific pathways; inhibition of certain enzymes is shown to interfere with oncogenic signaling, and measurement of certain enzyme levels is correlated with patient survival. The present methods comprise measuring level of expression of at least one of the enzymes involved in glucose uptake or metabolism, wherein increased expression of the at least one of the enzymes relative to expression in a normal cell correlates with poor prognosis of disease in a patient. Preferably the genes whose expression level is measured include GLUT3, PFKP, GAPDH, ALDOC, LDHA and GFPT2. Also disclosed are embodiments directed towards downregulating the expression of some genes in glucose uptake and metabolism.

15 Claims, 29 Drawing Sheets

USE OF GLYCOLYTIC PATHWAYS FOR INHIBITING OR MEASURING ONCOGENIC SIGNALING

CROSS-REFERENCE TO RELATED APPLICATIONS

This application claims priority from U.S. Provisional Patent Application No. 61/698,213 filed on Sep. 7, 2012, which is hereby incorporated by reference in its entirety.

STATEMENT OF GOVERNMENTAL SUPPORT

This invention was made with U.S. Government support under Contract Number DE-AC02-05CH11231 between the U.S. Department of Energy and The Regents of the University of California for the management and operation of the Lawrence Berkeley National Laboratory. The U.S. Government has certain rights in this invention.

REFERENCE TO SEQUENCE LISTING, COMPUTER PROGRAM, OR COMPACT DISK

The instant application contains a Sequence Listing which has been submitted in ASCII format via EFS-Web and is hereby incorporated by reference in its entirety. Said ASCII file was created on Sep. 6, 2013, is named "2960_78_1_SeqList.txt" and is 2,5761 bytes in size.

BACKGROUND OF THE INVENTION

Field of the Invention

The present invention relates to the field of cancer diagnostics and therapy, especially with respect to glucose metabolism and oncogenesis.

Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

The glucose intermediary metabolism often has been referred to as a "housekeeping" function (Bissell, 1981), but the increase in aerobic glycolysis in cancer, referred to as the "Warburg effect", is creating much excitement again. The original hypothesis by Warburg stated that irreversible mitochondrial dysfunction is the underlying reason of the metabolic shift to aerobic glycolysis (Warburg, 1956). However, mitochondrial dysfunction is not always observed in cancer cells even when there is increased aerobic glycolysis (Bissell et al., 1976; Frezza and Gottlieb, 2009). The current literature views the metabolic alterations as a result of the pleiotropic response to oncogenic signaling, thus placing those pathways upstream of glycolytic metabolism (reviewed in: Kroemer and Pouyssegur, 2008; Levine and Puzio-Kuter, 2010; Vander Heiden et al., 2009). The most highly mentioned roles of increased glucose metabolism in cancer are contributions to the tumor's proliferation and survival. The glycolytic pathway is able to provide ATP independently of oxygen even when tumors confront a hypoxic microenvironment (Gatenby and Gillies, 2004). It is true that many intermediary glucose metabolites are utilized for diverse biosynthetic processes such as nucleotide and lipid syntheses (Vander Heiden et al., 2009). Also NADPH, a reducing equivalent generated by glucose metabolism, sequesters ROS and thus confers resistance to cell death (Bensaad et al., 2006; Vaughn and Deshmukh, 2008).

On the other hand, the idea that glucose levels trigger intra- and inter-cellular signaling has been accepted widely in the fields of diabetes and endocrinology. Glucose signaling has been shown to be linked to physiological and pathological events such as regulation of hormone secretion and "insulin resistance" (Marshall, 2006; Marty et al., 2007; Schuit et al., 2001). Intriguingly, Warburg theorized that the metabolic shift to glycolysis is "the origin of cancer cells" (Warburg, 1956). However, the demonstration of causative effects of the increased glucose metabolism itself on oncogenesis has eluded the field (see McKnight, 2010).

There is now broad recognition of the universality of increased aerobic glycolysis in cancer. Given the demonstration of the impact of the microenvironment, including the composition of the medium (Bissell, 1981), on gene expression and integration of signaling events observed in 3D organotypic assays in laminin-rich extracellular matrix gels (lrECM; summarized in Bissell et al., 2005), we hypothesized that glucose uptake and metabolism would be an integral component of the tissue integration plan. We reasoned that if uptake and metabolism of glucose were hyperactivated, by mutation or increased levels of glucose in tissues and/or media, other oncogenic pathways could be activated reciprocally. Here we directly address this important but neglected possibility in cancer promotion using 3D lrECM cultures where both malignant and nonmalignant breast cells behave phenotypically as if they were in vivo (Petersen et al., 1992).

Described below are methods utilizing the present findings that inhibition of glucose uptake or metabolism suppresses the known oncogenic pathways and results in "phenotypic reversion" in a number of breast cancer cells. Significantly, forced increase in glucose uptake (and thus metabolism) in the examples below activated some of the other signaling pathways involved in oncogenesis, leading to a disorganized and malignant-like phenotype in non-malignant breast cells. We show that both the glycolytic pathway and the hexosamine biosynthetic pathway (HBP) are involved in the reciprocal regulation. Our findings suggest strongly that increased glucose uptake and metabolism in non-malignant cells compared to normal unstressed cells could be an oncogenic event analogous to activation of EGFR, β1 integrin, PI3K-Akt or MEK-ERK. We also unravel mechanisms of the intricate and hitherto unknown reciprocal activation by which glucose metabolism directly integrates with the other signaling pathways in 3D.

SPECIFIC PATENTS AND PUBLICATIONS

Itoh M, Nelson C M, Myers C A, Bissell M J. (2007) Rap1 integrates tissue polarity, lumen formation, and tumorigenic potential in human breast epithelial cells. Cancer Res. 67(10):4759.

BRIEF SUMMARY OF THE INVENTION

The following brief summary is not intended to include all features and aspects of the present invention, nor does it imply that the invention must include all features and aspects discussed in this summary.

The present invention comprises methods for measuring and/or inhibiting the oncogenic status of a cell, based on a newly found role of increased glucose uptake in activating oncogenic signaling and the disruption of tissue polarity, compared to a reference cell, such as a normal human primary cell in culture. By mimicking in vivo conditions with 3D cell culture, a reciprocity in glycolytic and oncogenic signaling was determined. It is shown here experimentally that that inhibition of glucose uptake or metabolism suppresses the known oncogenic pathways and results in "phenotypic reversion" in a number of breast cancer cells. Both the glycolytic pathway and the hexosamine biosynthetic pathway (HBP) are involved in the reciprocal regulation. Thus, platelet-type phosphofructokinase (PFKP), glyceraldehyde-3-phosphate dehydrogenase (GAPDH), aldolase (ALDO) and lactate dehydrogenese A (LDHA) are now known to be up-regulated in oncogenic cells, with GLUT3, a facilitative glucose transporter, showing the most dramatic up-regulation. These markers may be measured to assess the oncogenic status of a cell. One may conveniently measure expression level by protein assay such as ELISA, and determine increase by reference to a normal cell of comparable phenotype.

Inhibition of glucose metabolism such as by using 2-deoxy-D-glucose (2DG) induced phenotypic reversion, suggesting that inhibition of this pathway will inhibit oncogenesis. Knockdown of GLUT3 sensitized carcinoma cells more significantly to the reduction in glucose level, suggesting that increased uptake mediated by high expression of the glucose transporter is for maintaining the malignant phenotype. Inhibitors of GAPDH and LDH were found to validate the finding that the metabolic reactions between GAPDH and LDH are involved in malignant progression.

In examining human breast cancer patient microarray data, it was found that significant correlation between poor prognosis and higher expression of glycolytic enzymes (PFKP, ALDOC, GAPDH, LDHA, GLUT3, or GFPT2) compared to expression levels in a normal cell.

Thus, the present invention, in certain aspects, comprises a method for evaluating a level of oncogenic signaling in a cell, wherein one can determine oncogenic potential from increased signaling by looking for increased expression levels of a glycolytic enzyme, such as (i) platelet-type phosphofructokinase (PFKP), (ii) glyceraldehyde-3-phosphate dehydrogenase (GAPDH), (iii) aldolase (ALDO) or (iv) lactate dehydrogenase A (LDHA); one may also find such oncogenic potential in a glucose transporter such as GLUT3. One may also find such potential in increased level of expression of an enzyme in the hexosamine biosynthetic pathway (HBP), such as glucosamine-fructose-6-phosphate aminotransferase 2 (GFPT2). As is known in the art, expression level may be detected by assaying transcription (mRBNA) or protein expression by specific protein assays applied to a test cell and a reference cell.

In certain aspects, the method further comprises measuring the expression level of at least one of epidermal growth factor receptor (EGFR) and integrin beta 1 (ITGB1). The method may also comprise measuring the expression level of Glucose transporter type 3, (SLC2A3, hereinafter "GLUT3"). The expression level is determined by measuring the expression of mRNA encoding the protein. The expression level may further be determined by measuring the expression of genes on a microarray.

The present invention also comprises methods used to evaluate prognosis of breast cancer in patients comprising: obtaining a tumor cell, and measuring the expression level of at least one of (a) a glycolytic enzyme selected from the group consisting of platelet-type phosphofructokinase (PFKP), glyceraldehyde-3-phosphate dehydrogenase (GAPDH), aldolase (ALDO) and lactate dehydrogenese A (LDHA); (b) a glucose transporter; and (c) glucosamine-fructose-6-phosphate aminotransferase 2 (GFPT2) wherein an increased expression correlates with poor prognosis of breast cancer. In certain aspects, the method may further comprise measuring the expression level of at least one of epidermal growth factor receptor (EGFR) and integrin beta 1 (ITGB1).

The present invention also comprises methods for increasing survival time in a patient with a malignant tumor, comprising the step of inhibiting one of glutamine-fructose-6-phosphate transaminase (GFPT), O-linked N-acetylglucosamine (O-GlcNAc) transferase (OGT), fructose-6-phosphate amidotransferase (GFAT), soluble adenylyl cyclase (sAC) and Glucose transporter type 3, (GLUT3). In some aspects, the malignant tumor is a breast cancer tumor. In certain aspects, the present method further comprises the step of inhibiting at least one of glutamine-fructose-6-phosphate transaminase (GFPT), Glucose transporter type 3, (GLUT3) and OGT.

The inhibitor used is selected from the group consisting of a chemical inhibitor, an antibody and an antisense RNA molecule, including siRNA.

The present invention also comprises a synthetic oligonucleotide inhibitor of expression of one of (a) glutamine-fructose-6-phosphate transaminase (GFPT); (b) O-linked N-acetylglucosamine (O-GlcNAc) transferase (OGT); (c) fructose-6-phosphate amidotransferase (GFAT); and (d) soluble adenylyl cyclase (sAC) and Glucose transporter type 3, (GLUT3).

The present invention also relates to a method of suppressing a malignant phenotype in a cell comprising providing to said cell a synthetic oligonucleotide complementary to mRNA of one of glutamine-fructose-6-phosphate transaminase (GFPT), O-linked N-acetylglucosamine (O-GlcNAc) transferase (OGT), fructose-6-phosphate amidotransferase (GFAT), soluble adenylyl cyclase (sAC) and Glucose transporter type 3, (GLUT3).

BRIEF DESCRIPTION OF THE DRAWINGS

FIG. 8A, 8B, 8C, 8D, 8E, FIG. 8F, 8G, 8H, 8I, FIG. 8J and FIG. 8K, 8L, 8M, 8N is a series of images and graphs showing that the sAC-EPAC1-Rap1 pathway is responsible for glycolysis-mediated upregulation of β1 integrin and loss of acinar polarity. Epac is a guanine nucleotide exchange factor for the small GTPase Rap.

DETAILED DESCRIPTION OF THE PREFERRED EMBODIMENT

Definitions

Figure 1:
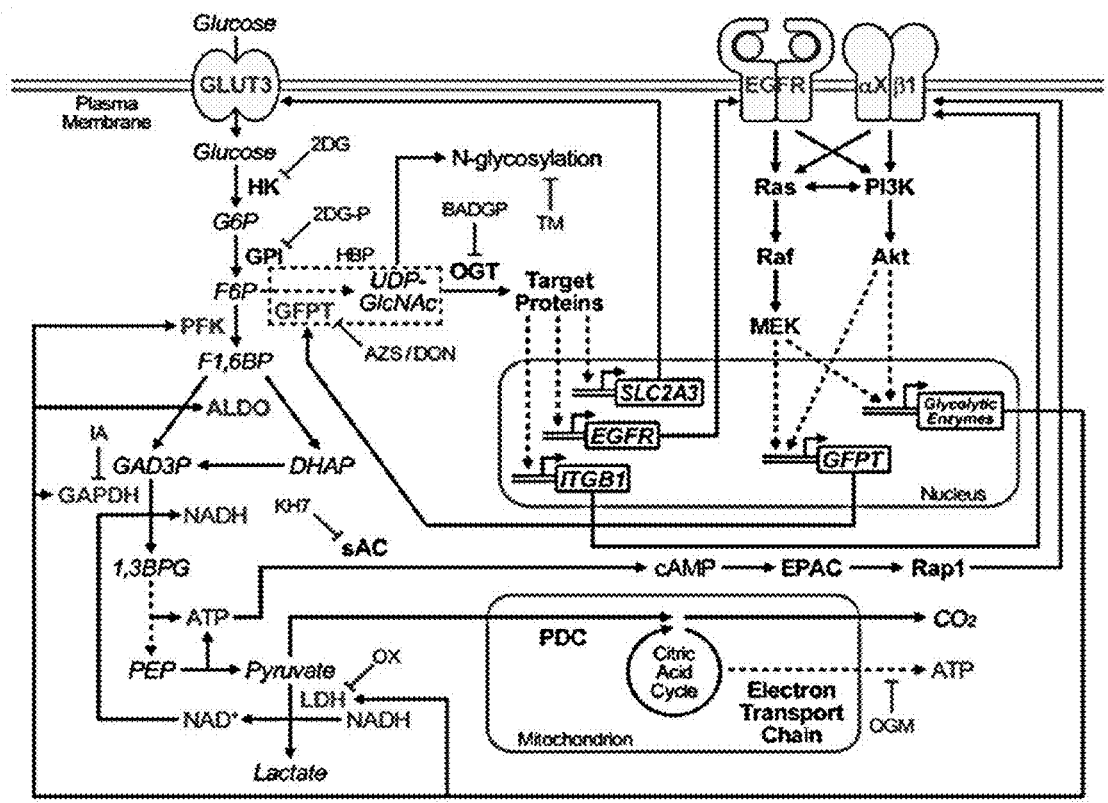
FIG. 1 is a schematic representation showing reciprocal interactions between increased glucose uptake/metabolism and other signaling pathways.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "three dimensional (3D) cell culture" as used herein refers to culturing cells in 3D gels as a surrogate for normal tissue so as to recapitulate both the 3D organization and multicellular complexity of an organ. The 3D cell cultures range from simple monotypic cultures to 3D co-cultures containing multiple cell types, which approximate organ structure and function in vitro. In their most simplistic form, they comprise homogeneous epithelial cell populations that are cultured within 3D basement membrane-like matrices. 3D cell cultures are important in understanding the molecular mechanisms involved in how gene expression is regulated by changes in the microenvironment. The tissue microenvironment is composed of an interactive network of soluble growth factors, extracellular matrix (ECM) components and neighboring cells. 3D cultures use a variety of matrices comprising ECM components including collagen, basement membrane and reconstituted basement membrane (from different cell types such as skin, pancreas, lung, liver, mammary gland). Another commonly used matrix is reconstituted basement membrane derived from the Englebreth-Holm-Swarm (EHS) mouse sarcoma tumor (Petersen et al, 1992 "Interaction with basement membrane serves to rapidly distinguish growth and differentiation pattern of normal and malignant human breast epithelial cells", PNAS, 1992, vol. 89, pages 9064-9068), which is available commercially as Matrigel or Cultrex. In the present disclosure 3D cell culture is used interchangeably with 3D lrECM culture, where lr stands for laminin-rich. We refer to any extracellular matrix gel rich in laminin-111 including the commercial products Matrigel™ and Cultrex® as lrECM. For establishing a 3D culture, cells are dispersed and embedded into the ECM gel and used for assays upon incubation. Details of 3D cultures and assays may be obtained from Genee Y. Lee, et al. ("Three-dimensional culture models of normal and malignant breast epithelial cells", Nature Methods 1997, vol 4, pages 359-365). 3D cell cultures are useful in distinguishing between normal (including pre-malignant) and malignant cells. Petersen et al (1992) showed that normal human breast epithelial cells embedded in lrECM as single cells were able to form multicellular spherical colonies with a final size close to that of true acini in situ and with correct tissue polarity and were growth-arrested; while the malignant cells continued to grow, piled up and formed large disorganized tumor-like colonies.

The term "tumor reversion" as used herein refers to a phenomenon in which invasive and metastatic cancer cells revert to a near-normal phenotype. Weaver et al ("Reversion of the malignant phenotype of human breast cells in three-dimensional culture and in vivo by integrin blocking antibodies", J. Cell Biol., vol. 137, pages 231-245, Apr. 7, 1997) observed when 3D cultures of tumor cells were treated with antibodies to block β1 integrin function, the tumor cells phenotypically reverted by forming organized polarized and growth arrested colonies comparable to that of non-malignant cells. Such effect is observed in 3D cultures not in cells cultured as 2D monolayers. Reversion may be caused by single inhibitors or by sets of inhibitors applied in tandem. In human breast epithelial cell, reversion to a near normal phenotype is defined by the formation of small, growth-arrested, well-differentiated, and polarized acinar structures in 3D cultures. As discussed below, inhibiting oncogenic signaling may bring about tumor reversion.

The term "GFPT" as used herein refers to the gene family encoding glutamine-fructose-6-phosphate transaminase, the rate limiting enzyme in hexosamine biosynthesis. GFPT controls the flux of glucose into the hexosamine pathway and catalyzes the formation of glucosamine 6-phosphate. GFPT includes genes and gene products of GFPT1 HUGO gene ID HGNC:4241, ad GFPT2.

The term "ITGB1" as used herein refers to the gene encoding the integrin β1 in humans. Integrins are heterodimeric proteins made up of alpha and beta subunits. The protein encoded by this gene is a beta subunit. Six alternatively spliced variants have been found for this gene that encodes five proteins with alternate carboxy termini. At least 18 alpha and 8 beta subunits of integrins have been described in mammals. Integrin family members are membrane receptors involved in cell adhesion and recognition in a variety of processes including embryogenesis, hemostasis, tissue repair, immune response and metastatic diffusion of tumor cells.

The term "EGFR" as used herein refers to epidermal growth factor receptor. EGFR is a transmembrane tyrosine kinase and the cell-surface receptor for members of the epidermal growth factor family (EGF-family) of extracellular protein ligands. The epidermal growth factor receptor is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). Mutations affecting EGFR expression or activity could result in cancer. EGFR dimerization stimulates its intrinsic intracellular protein-tyrosine kinase activity. As a result, autophosphorylation of several tyrosine (Y) residues in the C-terminal domain of EGFR occurs. This autophosphorylation elicits downstream activation and signaling by several other proteins that associate with the phosphorylated tyrosines through their own phosphotyrosine-binding SH2 domains. These downstream signaling proteins initiate several signal transduction cascades, principally the MAPK, Akt and JNK pathways, leading to DNA synthesis and cell proliferation. Such proteins modulate phenotypes such as cell migration, adhesion, and proliferation. EGFR is required for normal mammary development and lactation. EGFR is expressed aberrantly in ≈40% of breast carcinomas, particularly those with a poor prognostic and an invasive phenotype, and currently is being explored as a potential target for cancer therapy. Wang et al (PNAS 1998, vol 95: pages 14821-26) have shown that EGFR is overexpressed in the tumorigenic T4-2 cells but is significantly down-regulated when these cells are reverted phenotypically by the β1-integrin function-blocking antibody. Conversely, treatment of T4-2 cells with an EGFR neutralizing antibody and an EGFR-specific inhibitor also induces phenotypic reversion and down-regulation of β1-integrin. This bidirectional cross-modulation of β1-integrin and EGFR pathways is induced by a 3D BM and is absent in monolayer (2D) cultures.

The term "glucose transporter" as used herein refers to the protein family of facilitative glucose transporters which comprises 14 isoforms that share common structural features such as 12 transmembrane domains, N- and C-termini facing the cytoplasm of the cell, and a N-glycosylation side either within the first or fifth extracellular loop. Based on their sequence homology, three classes can be distinguished: class I includes GLUT1-4 and GLUT14, class II the "odd transporters" GLUT5, 7, 9, 11, and class III the "even transporters" GLUT6, 8, 10, 12 and the proton driven myoinositol transporter HMIT (or GLUT13). Further details are given in Zhao F Q, Keating A F, Curr Genomics. 2007 April; 8(2): 113-28, "Functional properties and genomics of glucose transporters."

The term "GLUT3" as used herein refers to glucose transporter type 3, a high-affinity isoform of Type I glucose transporter that is mostly expressed in neurons, where it is believed to be the main glucose transporter isoform. It is also expressed in the placenta. The GLUT3 protein is encoded by the gene denoted by GLUT3, SLC2A, etc.

The term "ALDO" as used herein refers to an enzyme catalyzing the reversible aldol condensation of dihydroxyacetone phosphate (DHAP) and glyceraldehyde-3-phosphate (GA3P) to fructose-1,6-bisphosphate (F1,6BP). Due to their sequence homologies, three isoforms are found in the class I fructose-bisphosphate aldolase gene family, including Aldolase A (ALDOA), fructose-bisphosphate Aldolase B (ALDOB), and Aldolase C fructose-bisphosphate (ALDOC). More information may be found in Tolan et al., "Evolutionary implications of the human aldolase-A, -B, -C, and pseudogene chromosome locations," Am J Hum Genet. 1987 November; 41(5): 907-924.

The term "glycolysis" as used herein refers to the metabolic pathway that converts glucose $C_6H_{12}O_6$, into pyruvate, $CH_3COCOO^- + H^+$. The free energy released in this process is used to form the high-energy compounds ATP (adenosine triphosphate) and NADH (reduced nicotinamide adenine dinucleotide). The definite sequence of ten reactions involving ten intermediate compounds (one of the steps involves two intermediates) is known. The enzymes involved are hexokinase, phosphoglucose isomerase; phosphpfructose kinase; aldolase; triose phosphate isomerase; glyceraldehyde phosphate dehydrogenase; phosphoglycerate kinase; phosphoglycerate mutase; enolase; andpyruvate kinase. The three regulated enzymes in the pathway are hexokinase, phosphofructokinase, and pyruvate kinase.

Malignant rapidly-growing tumor cells typically have glycolytic rates that are up to 200 times higher than those of their normal tissues of origin. This phenomenon was first described in 1930 by Otto Warburg and is referred to as the Warburg effect. The Warburg hypothesis claims that cancer is primarily caused by dysfunctionality in mitochondrial metabolism, rather than because of uncontrolled growth of cells. A number of theories have been advanced to explain the Warburg effect. This high glycolysis rate has important medical applications, as high aerobic glycolysis by malignant tumors is utilized clinically to diagnose and monitor treatment responses of cancers by imaging uptake of 2-18F-2-deoxyglucose (FDG) (a radioactive modified hexokinase substrate) with positron emission tomography (PET).

The term "hexosamine biosynthetic pathway" (HBP) as used herein refers to the pathway that results in the production of UDP-N-acetylglucosamine (UDP-GlcNAc) and other nucleotide hexosamines. UDP-GlcNAc, the major product, is the unique donor for the O-linkage of a single N-acetylglucosamine molecule (O-GlcNAc) to many cytoplasmic and nuclear proteins. Upon entering the cell glucose is rapidly phosphorylated to glucose-6-phosphate which can be oxidized via glycolysis or the pentose phosphate shunt or stored as glycogen. In glycolysis, G6P is isomerized to fructose-6-phosphate (F6P) before the pathway proceeds. Approximately 2-5% of F6P, and for this matter glucose, is diverted to HBP. GFPT1 catalyzes the formation of glucosamine-6-phosphate with glutamine as an amine donor and F6P as an acceptor substrate in the first and rate limiting step of the pathway. Subsequently, the addition of an acetyl group yields N-acetyl glucosamine-6-phosphate which is rapidly modified to UDP-GlcNAc. The utilization of glucosamine and of acetyl in the first two steps potentially links amino acid and fatty acids metabolism with HBP. The glycolysis pathway and the hexosamine pathway, provides two possible fates for glucose. The majority of glucose will enter the glycolysis pathway, with a small percent entering the hexosamine pathway. However, with an excess of glucose in the bloodstream, more glucose will be taken up by the cells, resulting in the increase formation of UDP-glucosamine.

The HBP is illustrated in Endocrinology 141(6) 1922-1925 (2000).

The HBP receives approximately 1-3% of incoming glucose via the conversion of fructose-6-phosphate (Fru-6-P) to glucosamine-6-phosphate by the rate-limiting enzyme glutamine:fructose-6-phosphate amidotransferase (GFAT).

The term "breast tumor" as used herein refers to cancer originating from breast tissue, most commonly from the inner lining of milk ducts or the lobules that supply the ducts with milk. Cancers originating from ducts are known as ductal carcinomas; those originating from lobules are known as lobular carcinomas.

The term "prognosis" as used herein refers to a prediction of outcome and the probability of progression-free survival (PFS) or disease-free survival (DFS). These predictions are based on experience with breast cancer patients with similar classification. A prognosis is an estimate, as patients with the same classification will survive a different amount of time, and classifications are not always precise. Survival is usually calculated as an average number of months (or years) that 50% of patients survive, or the percentage of patients that are alive after 1, 5, 15, and 20 years. Prognostic factors include staging, (i.e., tumor size, location, grade, whether disease has spread to other parts of the body), recurrence of the disease, and age of patient. Prognosis is important for treatment decisions because patients with a good prognosis are usually offered less invasive treatments, such as lumpectomy and radiation or hormone therapy, while patients with poor prognosis are usually offered more aggressive treatment, such as more extensive mastectomy and one or more chemotherapy drugs.

The term "oncogenesis" or "oncogenic" as used herein refers to the creation of cancer. It is a process by which normal cells are transformed into cancer cells. It is characterized by a progression of changes on cellular and genetic level that ultimately reprogram a cell to undergo uncontrolled cell division, thus forming a malignant mass. Oncogenesis is characterized by changes in cell adhesion, migration, and proliferation. The phrase "oncogenic signaling" is used in its conventional sense to refer to cell signaling pathways that lead to oncogenic transformation, i.e. the cancer phenotype.

The term "siRNA" (small interfering RNA) as used herein refers to a class of double stranded RNA molecules 20-25 nucleotides in length. siRNA is most notably involved in the RNA interference (RNAi) pathway where it interferes with the expression of a specific gene. siRNA also acts in RNAi-related pathways, e.g., as an antiviral mechanism or in shaping the chromatin structure of a genome. siRNAs can also be exogenously (artificially) introduced into cells by various transfection methods to bring about the specific knockdown of a gene of interest. In essence, any gene whose sequence is known can, thus, be targeted based on sequence complementarity with an appropriately tailored siRNA. siRNA can be directly introduced into a cell by microinjection or electroporation or through stable transfection with a plasmid encoding the appropriate sequence from which siRNAs can be transcribed, or by more elaborate lentiviral vector systems allowing the inducible activation or deactivation of transcription. When desired, the siRNA can be labeled to track the delivery and uptake of siRNA. The siRNA can be labeled with, for example, fluorescent dyes, or modified with various other modifications like 2'O methyl RNA, biotin or digoxigenin based on the need. siRNAs can be custom designed and synthesized commercially.

As described in detail below, the present invention comprises a method of suppressing a malignant phenotype in a cell comprising providing to said cell a synthetic oligonucleotide complementary to mRNA of one of glutamine-fructose-6-phosphate transaminase (GFPT), O-linked N-acetylglucosamine (O-GlcNAc) transferase (OGT), fructose-6-phosphate amidotransferase (GFAT), soluble adenylyl cyclase (sAC) and Glucose transporter type 3, (GLUT3). The synthetic oligonucleotide can be a siRNA, prepared, e.g., as described in US 2007/0032441, "Rna interference mediated inhibition of gene expression using chemically modified short interfering nucleic acid (sina)." The synthetic oligonucleotides may also be antisense oligonucleotides, antisense polynucleotides, deoxyribozymes, morpholino oligonucleotides, dsRNA, RNAi molecules, siRNA molecules, PNA molecules, DNAzymes, and 5'-end-mutated U1 small nuclear RNAs, or analogs of the preceding.

In certain embodiments, for example, the antisense compounds are antisense oligonucleotides that comprise naturally occurring nucleobases and an unmodified internucleoside linkage. In other embodiments, for example, the antisense compounds are antisense oligonucleotides comprising at least one modified internucleoside linkage, including those with a phosphorothioate linkage. Suitable antisense compounds also include, for example, oligonucleotides comprising at least one modified sugar moiety. Suitable antisense compounds also include, by way of example, oligonucleotides comprising at least one modified nucleobase.

The following Table 1 lists the abbreviations of the enzymes, pathways, inhibitors and metabolites referred to herein.

| Abbreviation | |
|---|---|
| Enzymes and Pathways | |
| HK | hexokinase |
| GPI | glucose-6-phosphate isomerase |
| PFK | phosphofructokinase |
| ALDO | aldolase |
| GAPDH | glyceraldehyde-3-phosphate dehydrogenase |
| LDH | lactate dehydrogenase |
| PDC | pyruvate dehydrogenase complex |
| GFPT | glutamine-fructose-6-phosphate transaminase |
| OGT | O-GlcNAc transferase |
| sAC | Soluble adenylylcyclase |
| HBP | hexosamine biosynthetic pathway |
| Chemical Inhibitors | |
| 2DG | 2-deoxy-D-glucose |
| IA | Iodoacetate |
| OX | Oxamate |
| AZS | Azaserine |
| DON | 6-diazo-5-oxonorleucine |
| BADGP | Benzyl-2-acetamido-2-deoxy-α-D-galactopyranoside |
| TM | Tunicamycin |
| OGM | Oligomycin |
| Metabolic Intermediates | |
| G6P | glucose-6-phosphate |
| F6P | fructose-6-phosphate |
| F1,6BP | fructose-1,6-bisphosphate |
| GAD3P | glyceraldehyde-3-phosphate |
| DHAP | dihydroxyacetone phosphate |
| 1,3BPG | 1,3-bisphosphoglycerate |
| PEP | phosphoenolpyruvate |
| GlcNAc | N-acetylglucosamine |

Overview

Despite the resurgence of interest in the role of aerobic glycolysis in cancer, increased glucose metabolism is viewed as a result of oncogenic insults needed for growth and survival. Using a 3D laminin-rich culture, here we show that the activation is reciprocal: A surge in glucose uptake and metabolism itself can activate known oncogenic signaling pathways including EGFR, β1 integrin, MEK and Akt. Importantly, overexpression of GLUT3 in non-malignant breast epithelial cells leads to loss of tissue polarity and a malignant phenotype through increase in glucose uptake. Reduction of glucose uptake by malignant cells allows formation of polar acini via suppression of EPAC-Rap1 signaling and O-linked N-acetyl glucosamine modification downstream of hexosamine biosynthetic pathway. Demonstration of reciprocal signaling integration in 3D elucidates the molecular mechanism by which increased glucose uptake and metabolism also could result in acquisition of malignant phenotype.

Further, it is shown that higher expression of glycolytic enzymes and other genes correlates with poor prognosis of breast cancer in patients. Higher expression of GFPT can also predict poor prognosis. Patient survival was plotted on survival curves, and it was shown that it can be predicted based on the gene expression of one of a group of genes encoding a glucose transporter, GFPT and the enzymes of glycolysis-PFK, GAPDH and LDH. Higher expression indicated less chance of survival over time.

The current literature on aerobic glycolysis has led to a number of important studies where the metabolic alteration is being targeted for the treatment of cancer (Chen et al., 2007; Kroemer and Pouyssegur, 2008). In clinical studies, by necessity, the emphasis is exclusively on tumor-killing and/or -suppressive effects of blockade of glucose metabolism. Other studies have been usually performed in 2D cultures which may explain why the direct effects of changes in glucose uptake and metabolism on oncogenic signaling have eluded the current literature as noted by McKnight (McKnight, 2010, also see below).

Figures 8A, 8B, 8C, 8D:
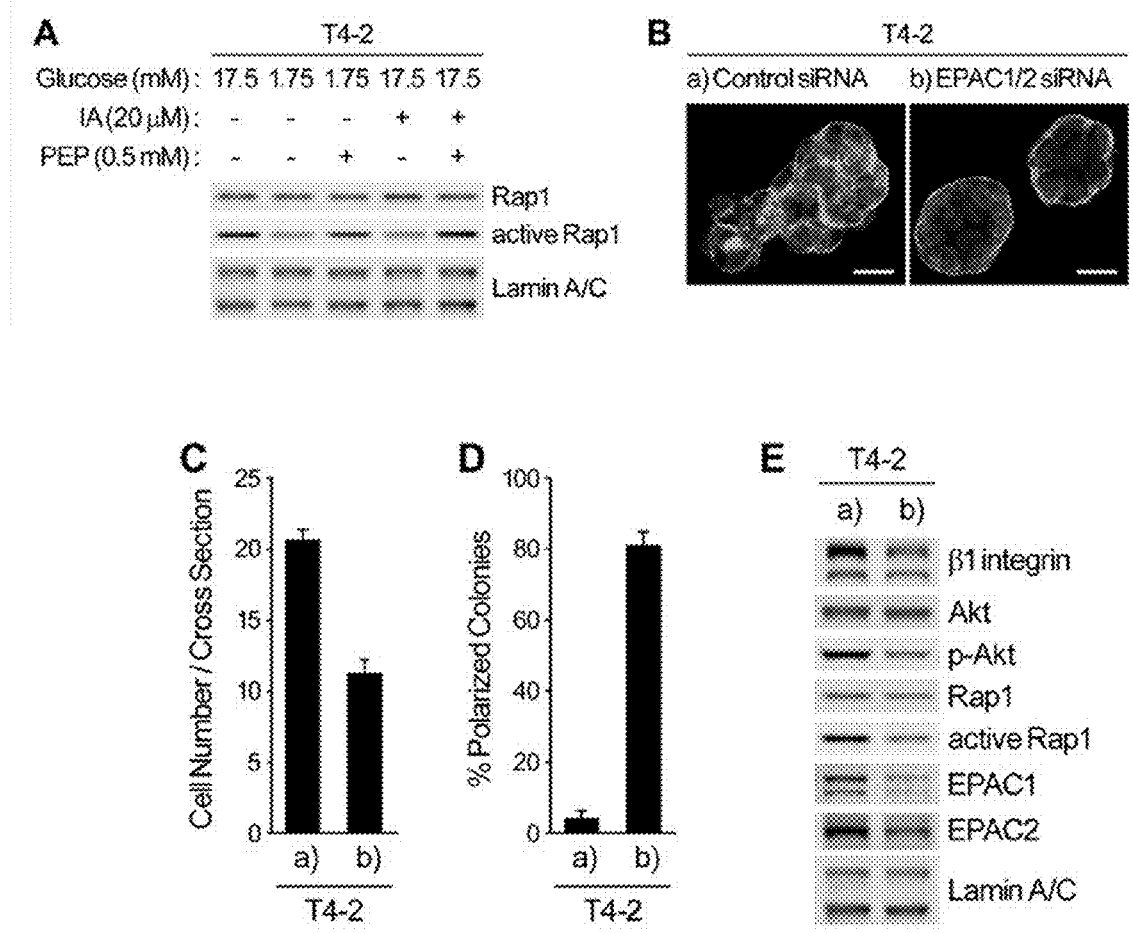

The work described herein shows that glucose metabolism in fact regulates key signaling pathways commonly activated in many types of cancers, and identifies two crucial pathways in glucose metabolism. The first is increase in metabolism between GAPDH and LDH which is required for increased β1 integrin expression and downstream Akt activity and its regulation by sAC-EPAC-Rap1 pathway (FIG. 8A-8N). Although the mechanisms by which Rap1 regulates β1 integrin expression and signaling still remain to be elucidated, another group has shown also that Rap1 regulates total level of β1 integrin expression in human colonic epithelial cells (Severson et al., 2009). The second pathway involves the finding that inhibition of HBP is sufficient to induce suppression of all oncogenic signaling measured including aerobic glycolysis, EGFR and β1 integrin signaling resulting in phenotypic reversion of tumor cells in 3D lrECM assay. GFPT, the rate-limiting enzyme of HBP, was shown to be regulated at transcriptional level downstream of several protein kinases such as Src, PKC, EGFR and MEK involved in oncogenic signaling in breast cancer but also in mesangial cells (James et al., 2001; Paterson and Kudlow, 1995). In our experiments, activities of EGFR and MEK as well as those of β1 integrin and Akt, were all required for increased GFPT expression in T4-2 cells (FIG. 10A-10I). However, PKC inhibitors, despite suppressing growth, were unable to revert the malignant phenotype (not shown).

Of the two HBP branches, inhibition of O-GlcNAcylation, but not the N-linked glycosylation, was sufficient for complete phenotypic reversion (FIG. 10A-10I). There was significant suppression of EGFR, β1 integrin and GLUT3 mRNA expression by inhibiting either HBP or O-GlcNAc signaling (FIGS. 10A-10I and 11A-11D). Whether this involves direct regulation of transcriptional activity by O-GlcNAc modification of transcriptional factors (Issad and Kuo, 2008) and/or modulation by O-GlcNAc modification of signaling intermediates and networks (Hart et al., 2007) remains to be elucidated.

These findings show how multiple feedback loops involving EGFR, β1 integrin, glycolytic pathway and HBP result in integration of metabolism with other signaling pathways (FIG. 1). Importantly, this reciprocity is 3D-specific: Treatment with the same inhibitors shown to revert the malignant phenotype of T4-2 cells in lrECM induced no obvious suppression of the key signaling activities (EGFR, β1 integrin, Akt and MEK) in 2D cultures.

The interdependence of form and function in regulation of glucose metabolism parallel our previous findings for other oncogenic signaling where integration occurs in the context of 3D architecture, but almost never in 2D monolayers (Bissell et al., 2005; Muthuswamy et al., 2001; Wang et al., 1998). In addition, despite the large differences in the GLUT3 levels between S1 and T4-2 cells in 2D (data not shown), there were little or no statistically significant differences in glucose uptake. Thus glucose metabolic pathways, just like other pathways known to be involved in oncogenesis, are exquisitely context-dependent.

It is important to note that the 3D culture systems using both rodents and human mammary cells were developed to allow analysis of molecular events and morphological properties with application to the in vivo situation (Barcellos-Hoff et al., 1989; Petersen et al., 1992). The data are essentially reproducible in mice (e.g. Park et al., 2008) and correlate well with findings in breast cancer patients (e.g. Fournier et al., 2006; Kenny and Bissell, 2007; FIG. 13A-13F). It is also relevant that the phenotypic reversion in 3D lrECM cultures is not simply due to growth arrest but to re-acquisition of tissue polarity and "homeostasis" (Weaver et al., 2002) allowing us precise investigation of the signaling integration plan (FIG. 7A-7K).

The mechanisms of glucose-triggered signaling have been widely investigated, although clear causative links to oncogenic events had not been delineated. The link between metabolic pathways and cellular (dys)functions has been best studied in glucose-sensing cells such as pancreatic β cells: Rise in ATP/AMP ratio by glucose metabolism leads to membrane depolarization by closure of ATP-sensitive $K^+$ channel, activation of voltage-dependent Ca2+ channel and secretion of insulin (reviewed in Schuit et al., 2001). In this context, Levin and colleagues (Litvin et al., 2003; Ramos et al., 2008) also invoke cAMP signaling: Their data indicate that due to the relatively low affinity of sAC for ATP, the enzyme activity is sensitive to cellular ATP concentration. Our data suggest that conversion of PEP into pyruvate, which is associated with ATP production, leads to Rap1 activation most probably through regulation of ATP-sensitive sAC-EPAC pathway (FIGS. 1 and 8A-8N). It is important to note that mitochondrial activity was not impaired in the tumor cells in lrECM; whether and how tumor cells link sAC function specifically to the ATP produced by glycolysis rather than by respiration is an emerging question of interest.

AMPK, mTOR and HBP have been referred to as the "well-established nutrient signaling pathways" (Marshall, 2006). However, whereas the roles of the first two pathways have been studied extensively in cancer (e.g. Shackelford and Shaw, 2009), functional roles of HBP has been investigated largely in diabetes. Overall, increase in the carbon flux into HBP was shown to suppress insulin-induced glucose uptake and increase storage of glucose as glycogen and lipids in adipose and muscle (reviewed in Marshall, 2006). It is important to note that functions of a signaling pathway are totally context-dependent and not necessarily the same in different (normal) tissues or when cells were transformed. Indeed, HBP seems to function differently in the transformed mammary epithelial cells. Our data show that HBP promotes, rather than inhibit, glucose uptake and metabolism in breast cancer cells when examined in 3D even in the presence of insulin (FIG. 10A-10I, see Experimental Procedures for culture condition). How cancer cells utilize the hexosamine signaling for different aspects of malignant phenotype including their pattern of metabolism (FIG. 10A-10I) is also an exciting question which should be addressed in the future.

Warburg's original hypothesis that aerobic glycolysis itself could be the "origin of cancer cells" (Warburg, 1956) has not been acknowledged directly. Our findings provide a hitherto undescribed proof for the direct role of increased aerobic glycolysis in inducing a cancer phenotype. Increased glucose uptake and metabolism themselves result in malignant progression since in a 3D context, as is the case in vivo, their activity dynamically and reciprocally regulates the other oncogenic pathways. These findings perhaps provide additional evidence for how metabolic diseases involving hyperglycemia, e.g. obesity and diabetes, could provide the microenvironment for higher risk of some cancers (summarized in Giovannucci et al., 2010; Hjartaker et al., 2008). Finally, the metabolic pathways identified here could provide additional targets for cancer therapy.

Assay Methods

As indicated by the following description, the present methods for determining a level of oncogenic activation, or a level of oncogenic signaling, can be carried out by a number of different assays. For example, assays of the relevant biomarkers of increased glucose metabolism that may lead to an oncogenic phenotype may be based on gene expression of the relevant markers, e.g. PFKP, GAPDH, ALDO, LDHA, GFPT, and GLUT3, or homologs or specific products thereof. mRNA levels of one of the foregoing markers may be measured. Exemplary methods for such measurement include microarray containing nucleic acids hybridizing to a cellular marker being measured. Such a microarray may be made and used as described below, and is commercially available, e.g. from Agilent Technologies (see, for example, SurePrint G3 Human Gene Expression Microarray, Agilent Catalog #G4851B).

In each methodology, determining whether an expression level is "increased" may be done by reference to a set of standard data from normal cells of the same phenotype (e.g. breast epithelial cells) or by performing the assay on a cell suspected of increased oncogenic signaling and a cell presumed to be normal, both cells being from the same individual and cultured under comparable conditions.

Other exemplary methods include Northern blotting, serial analysis of gene expression (SAGE), and reverse transcription polymerase chain reaction (rt-PCR).

Northern blotting is a technique used to measure gene expression by detecting RNA (or isolated mRNA) in a sample, which is described in Thomas et al., "Hybridization of denatured RNA and small DNA fragments transferred to nitrocellulose," PNAS, Vol. 77, No. 9, pp. 5201-5205 (1980). Briefly, in Northern blot analysis, RNA fragments separated by electrophoresis on an agarose gel are transferred onto one or more nitrocellulose membranes, incubated and detected with a suitable probe (see also U.S. Pat. No. 8,470,541).

Serial analysis of gene expression (SAGE) is further described in Velculescu et al, "Serial Analysis of Gene Expression," Science, Vol. 270, no. 5235, pp. 484-487 (20 Oct. 1995) and U.S. Pat. No. 5,695,937. This technique is based on the identification of and characterization of partial, defined sequences of transcripts corresponding to gene segments. These defined transcript sequence "tags" are markers for genes which are expressed in a cell, tissue, or an extract, for example. SAGE is based on several principles. First, a short nucleotide sequence tag (9 to 10 bp) contains sufficient information content to uniquely identify a transcript provided it is isolated from a defined position within the transcript. For example, a sequence as short as 9 bp can distinguish 262, 144 transcripts ($4^9$) given a random nucleotide distribution at the tag site, whereas estimates suggest that the human genome encodes about 80,000 to 200,000 transcripts (Fields, et al., Nature Genetics, 7:345 1994). The size of the tag can be shorter for lower eukaryotes or prokaryotes, for example, where the number of transcripts encoded by the genome is lower. For example, a tag as short as 6-7 bp may be sufficient for distinguishing transcripts in yeast. Second, random dimerization of tags allows a procedure for reducing bias (caused by amplification and/or cloning). Third, concatenation of these short sequence tags allows the efficient analysis of transcripts in a serial manner by sequencing multiple tags within a single vector or clone. As with serial communication by computers, wherein information is transmitted as a continuous string of data, serial analysis of the sequence tags requires a means to establish the register and boundaries of each tag. All of these principles may be applied independently, in combination, or in combination with other known methods of sequence identification. Improved techniques, such as LongSAGE, RL-SAGE, and SuperSAGE may also be used.

Reverse transcription polymerase chain reaction (rtPCR) is used to detect RNA expression levels by cloning expressed genes by reverse transcribing the RNA of interest into its DNA complement through the use of the reverse transcriptase enzyme. As disclosed in Schanke et al. WO 2000/071739, in RT-PCR, an RNA template is first copied into cDNA using a reverse transcriptase, a reaction termed "first-strand synthesis." PCR is then performed to exponentially amplify the cDNA (see U.S. Pat. Nos. 4,683,195 and 4,683,202). In its least sophisticated implementation, the RT-PCR method entails three steps, namely: (1) denaturation of the RNA by heating; (2) synthesis of the first cDNA strand ("first-strand synthesis") in a buffer containing, apart from the nucleoside triphosphates, a first primer capable of hybridizing with a sequence located in the vicinity of the 3' end of the RNA template, and a reverse transcriptase; and (3) synthesis of the second cDNA strand ("second-strand synthesis") by addition of a second primer capable of hybridizing with a sequence adjoining the 3' end of the first cDNA strand (i.e., the primer must be identical or sufficiently homologous to a sequence adjoining the 5' end of the RNA template) and a DNA polymerase, followed by the succession of PCR amplifications (Schwartz, S. J. Virol., 24(6): 2519-2529 (1990)). To attempt to address the technical problems often associated with RT-PCR, a number of protocols have been developed, where the above three step procedure has been reduced to a "two-step" (or "uncoupled") or a "one-step" (or "coupled") protocol.

Alternatively, protein levels of markers such as PFKP, GAPDH, ALDO, LDHA, GFPT, and GLUT3, or homologs thereof may be measured. This may be done. e.g., by antibody-based methods such as ELISA and Western blotting.

Enzyme linked immunosorbent assay (ELISA) is a quantitative in vitro test for an antibody or antigen (e.g., a bioagent) in which the test material is adsorbed on a surface and exposed to a complex of an enzyme linked to an antibody specific for the substance being tested for with a positive result indicated by a treatment yielding a color in proportion to the amount of antigen or antibody in the test material. This technique is described in U.S. Pat. No. 7,713,752 and the basic ELISA procedure is described more specifically, for one, in a book entitled Methods in Molecular Biology Vol. 42, John R. Crowther, Humana Press, 1995.

More recently, the foregoing definition for ELISA has been expanded beyond the colormetric approach, in which color and color intensity is used as the reporter or indicia of the antigen or antibody, to include a voltametric or amperiometric approach to detection and assay, in which the rate of change of voltage or current conductivity is proportional to the amount of antigen or antibody contained in the test material. Patent Cooperation Treaty application PCT/US98/16714, filed Aug. 12, 1998 (International Publication No. WO 99/07870), entitled "Electrochemical Reporter System for Detecting Analytical Immunoassay and Molecular Biology Procedures" (hereafter the "16714 PCT application"), claiming priority of U.S. patent application Ser. Nos. 09/105,538 and 09/105,539"), to which the reader may refer, describes both a colormetric and an electrochemical reporter system for detecting and quantifying enzymes and other bioagents in analytical and clinical applications. The electrochemical reporter system of the 16714 PCT application employs a sensor for detecting voltametric and/or amperiometric signals that are produced in proportion to the concentration of organic (or inorganic) reporter molecules by redox (e.g. reduction-oxidation) recycling at the sensor.

Western blotting is another technique used to detect protein levels in a sample. As described in U.S. Pat. No. 8,132,676, Western blotting involves the application of a protein sample (lysate) onto a polyacrylamide gel, subsequent separation of said complex mixture by electrophoresis, and the transfer or "electro-blotting" of separated proteins onto a second matrix, generally a nitrocellulose or polyvinylidene fluoride (PVDF) membrane. Following the transfer, the membrane is "blocked" to prevent nonspecific binding of antibodies to the membrane surface. Many antibody labeling or tagging strategies are known to those skilled in the art. In the simplest protocols, the transferred proteins are incubated or complexed with a primary enzyme-labeled antibody that serves as a probe. After blocking non-specific binding sites a suitable substrate is added to complex with the enzyme, and together they react to form chromogenic, chemiluminescent, or fluorogenic detectable products that allow for visual, chemiluminescence, or fluorescence detection, respectively. The most sensitive detection schemes make use of chemiluminescent or fluorescent phenomena. In chemiluminescent detection, an enzyme-substrate complex produces detectable optical emissions (chemiluminescence). These emissions are recorded and measured using suitable detectors such as film or photonic devices. Absence or presence of signal indicates whether a specific protein is present in the lysate, and signal intensity is related to the level of the protein of interest, which in some cases may be quantifiable.

Protein levels may also be determined by use of isotope-coded affinity tags (ICAT). This technique is described in detail in Glygi et al., "Quantitative analysis of complex protein mixtures using isotope-coded affinity tags," Nature Biotechnology 17:994-999 (1999). Briefly, as described there, the method uses a reagent that includes an affinity tag (biotin), which is used to isolate ICAT-labeled peptides; a linker that can incorporate stable isotopes; and a reactive group with specificity toward thiol groups (cysteines). The reagent exists in two forms, heavy (contains eight deuteriums) and light (contains no deuteriums). Two protein mixtures representing two different cell states (e.g. high glucose metabolism and normal glucose metabolism) have been treated with the isotopically light and heavy ICAT reagents, respectively; an ICAT reagent is covalently attached to each cysteinyl residue in every protein. The protein mixtures are combined and proteolyzed to peptides, and ICAT-labeled peptides are isolated utilizing the biotin tag. The mixture is analyzed by LC-MS. These peptides are separated by microcapillary high-performance liquid chromatography. A pair of ICAT-labeled peptides are chemically identical and are easily visualized because they essentially coelute, and there is an 8 Da mass difference measured in a scanning mass spectrometer (four m/z units difference for a doubly charged ion).

Experimental Procedures

Cell Culture on 2D and in 3D

HMT-3522 cells were cultured on tissue culture plastic (2D) and in 3D lrECM gels with H14 medium, a 1:1 mix of DMEM/F12 (UCSF Cell Culture Facility) supplemented with 250 ng/ml insulin, 10 µg/ml transferrin, 2.6 ng/ml sodium selenite, 0.1 nM β-estradiol, 1.4 µM hydrocortisone and 5 µg/ml prolactin but no serum. S1 cells were additionally supplemented with 10 ng/ml EGF. MDA-MB-231 and HCC70 cells were cultured in DMEM and RPMI1640, respectively, and were supplemented with 10% fetal bovine serum (FBS).

For 3D lrECM cultures, S1 and T4-2 cells were seeded at 840,000 and 600,000 cells per cm3 respectively in lrECM gel (Cultrex), overlaid with H14 medium. MDA-MB-231 and HCC70 cells were seeded at 625,000 cell per cm3 and overlaid with H14 medium supplemented with 1% FBS. Cells were used for each assay after 10 days, unless otherwise indicated.

For experiments that need to be done in shorter-term (e.g. cultures of siRNA-transfected cells or for live imaging), cells were seeded at 60,000 cells per cm2 on top (3D-OT) of lrECM gels overlaid with H14 medium containing 5% (v/v) lrECM. Cells were harvested after 3 days.

Chemicals, Inhibitory Antibodies and Metabolic Intermediates

Chemicals and inhibitory antibodies were as follows: anti-β1 integrin antibody clone AIIB2 (Aragen Bioscience), anti-EGFR antibody clone mAb225 (Oncogene), AG1478, LY294002, GM6001 (Calbiochem), PD98059 (New England Biolabs), KH7 (Cayman Chemical). All other reagents and metabolic intermediates were purchased from Sigma-Aldrich.

Protein Knockdown by siRNA Transfection

Predesigned siRNA duplexes targeting GLUT3, GFPT1, GFPT2 and OGT, as well as control siRNA were obtained from Ambion. The other siRNA duplexes were chemically synthesized and purchased from Hokkaido System Science. The sequences are as follows:

```
GAPDH,
                                     (SEQ ID NO: 1)
5'-GAGCCACAUCGCUCAGACAdTdT-3'
and
                                     (SEQ ID NO: 2)
5'-UGUCUGAGCGAUGUGGCUCdGdG-3';

EPAC1,
                                     (SEQ ID NO: 3)
5'-CCAUCAUCCUGCGAGAAGAdTdT-3'
and
                                     (SEQ ID NO: 4)
5'-UCUUCUCGCAGGAUGAUGGdTdG-3';
```

```
EPAC2,
                                          (SEQ ID NO: 5)
5'-GAGUUAGCAGGUGUUCUCAdTdT-3'
and (SEQ ID NO: 6)
5'-UGAGAACACCUGCUAACUCdTdC-3';

sAC,
                                          (SEQ ID NO: 7)
5'-AUGUAGCCUGGAGAUCCAUdTdT-3'
and (SEQ ID NO: 8)
5'-AUGGAUCUCCAGGCUACAUdTdT-3'.
```

In one embodiment, the siRNA duplexes may have an overhang of 1 to 5 nucleotides at the 3' end, 5' end, or both ends. Alternatively, it may have a blunt end truncated at both ends. The nucleotides of the overhang may be any sequence, but it may have 2 natural or non-natural nucleobases (i.e. purine or pyrimidine), or any combination thereof, each joined to a deoxyribose molecule attached thereto. For example, in one embodiment, the overhang may contain 2 dTs (deoxythymidine).

For transfection of each siRNA into T4-2 cells, Lipofectamine RNAi MAX (Invitrogen) was used, according to the manufacturer's instruction. Cells were trypsinized 36 hrs after transfection and cultured in 3D-OT lrECM for 3 days before harvest.

Assays of Glucose Uptake, Lactate Production and Mitochondrial Activity Assays

Cells suspended in 200 μl lrECM were seeded in 12 well glass-bottom plates (14 mm diameter; MatTek Corporation). Gels were overlaid with 500 μl H14 media and cultured for 10 days before each assay unless otherwise described.

For glucose uptake assay, cells were incubated with 1 μM of IRDye800CW-2DG (LI-COR Biosciences) for 1 hour, fixed within gels with 4% paraformaldehyde (PFA) in PBS for 30 min. and stained with DRAQ5 (1:10000 dilution), an infrared dye that binds stoichiometrically to DNA, for 30 min. Cells were extensively washed with PBS, then IRDye800-2DG uptake together with DRAQ5 staining were measured by using Odyssey Infrared Imaging System (LI-COR Biosciences).

For lactate production, on day 9, conditioned-media were harvested to measure lactate remaining in the 200 μl of the gel (assuming equilibrium between medium and gel, C0 nmol/μl). At this point 500 μl fresh H14 medium, which does not include lactate, was added. After 24 hours, total culture medium was harvested for measurement of final lactate concentrations (C nmol/μl) and total volumes (V μl) of the conditioned-media, and the cells in gel were fixed with PFA as above. Concentration of lactate in each sample was measured using a lactate assay kit (BioVision). Net lactate production within 24 hours (N) was calculated as follows: N=C×(V+200)−C0×200. Fixed cells were stained with DRAQ5, to measure total level of DNA as a surrogate for number of cells, and the staining was measured as above.

For mitochondrial activity, we slightly modified the method described previously (Morici et al., 2007). Briefly, cells were incubated with 2 μM MitoTracker® Orange CM-H2 TMRos (Invitrogen) for 1 hour and fixed with PFA as above. Cells were counterstained with Hoechst 33342 (Invitrogen), which is known also to bind to DNA stoichiometrically, then MitoTracker and Hoechst staining were measured by taking z-section images from top to bottom of the gels using confocal microscopy.

In each assay, one well, containing only lrECM, was made for background measurements. Glucose uptake measured by 2DG uptake, lactate production and MitoTracker staining were normalized using total DNA levels, and presented relative to that of control (either S1 or non-treated T4-2 cells).

Construction of GLUT3-Expressing Lentivirus Vector

HIV 5' LTR sequence in pTRIPZ vector (Open Biosystems) was removed by FspI-BbvCI digestion to replace with sequence containing chimeric CMV promoter-HIV 5' LTR. CMV promoter was amplified by PCR from pcDNA3 (Invitrogen), fused to sequence containing partial HIV 5' LTR sequence. The resulting intermediate vector, pTRIPZ-OY (optimal yield) was digested with BbvCI and NotI, to remove sequence containing TRE-minCMV promoter, turboRFP, UbqC promoter and rtTA3 (described in the manual provided by the manufacturer). The sequences containing EF1α/HTLV hybrid promoter and multiple cloning sites were removed from pCDH-EF1-MCS-T2A-Puro vector (System Bioscience) by digestion with the same restriction enzymes, and ligated into the digested pTRIPZ-OY vector, resulting in pLETIP vector. GLUT3 cDNA fused to C-terminal HA tag was amplified from total cDNA of T4-2 cells by PCR. The primers used were as follows: 5'-CGGGATC-CGCCACCATGGGGACACAGAAGGTCAC-3' (SEQ ID NO: 9) and 5'-AACCCGGGTCAAGCATAATCTG-GAACATCGTATGGATAGACATTGGTGGTGGTCTCC TTAGCA-3' (SEQ ID NO: 10). The amplified cDNA was digested with BamHI and XmaI, and ligated into the same sites of pBluescriptII SK(−) vector for validating the sequence. GLUT3-HA cDNA was then digested with BamHI and SmaI, and ligated into pLETIP vector digested with NotI, blunted with T4 polymerase and further digested with BamHI, resulting in pLETIP GLUT3-HA vector.

Establishment of S1 Cells Overexpressing GLUT3

The above-described pLETIP GLUT3-HA (or empty vector), together with plasmid vectors encoding VSV-G, HIVgp and Rev, were transfected into 293T cells, using polyethylenimine solution. Supernatants were collected and clarified with filtration (0.45 μm pore), and the virus particles were precipitated by ultracentrifugation. S1 cells were infected with the purified virus particles, using ExpressMag Transduction System (Sigma-Aldrich). After 48 hrs, cells were selected with 1 μg/ml puromycin for 7 days. Bulk clones were grown and expanded in H14 media (containing EGF) supplemented with 0.5 μg/ml puromycin for each assay.

Indirect Immunofluorescence

Pieces of lrECM gel containing cell colonies were suspended in approximately the same volume of phosphate buffered saline (PBS) and directly spread on glass slides. After brief air-drying, colonies were fixed with 3.7% paraformaldehyde (PFA) in PBS at room temperature (RT) for 10 min, washed with PBS containing 0.1 mM glycine, and permeabilized with 1:1 methanol/acetone at −20° C. for 10 min. After blocking with IF buffer (0.2% Triton X-100, 0.1% BSA [radioimmunoassay grade], 0.05% Tween 20, 7.7 mM NaN3 in PBS) containing 10% goat serum and 1% goat F(ab')2 anti-mouse immunoglobulin G (IgG; Caltag) at RT for 30 min, colonies were stained with anti-α6 integrin antibody (Chemicon International) at 4° C. overnight. Colonies were washed extensively with IF buffer, and stained with Alexa 568-labeled anti-rat IgG antibody at RT for 2 hr. Colonies were washed with IF buffer again, and nuclei were stained with DAPI at RT for 10 min. Slides were briefly washed with PBS and mounted with 50% glycerol in PBS.

Western Blotting

Cell colonies were separated from lrECM gels by shaking in PBS containing 5 mM EDTA and the proteinase inhibitor cocktail set I (Calbiochem) on ice for 30 min. Cells were lysed in lysis buffer (1% NP-40, 1% deoxycholate, 2% SDS, 150 mM NaCl, 20 mM Tris-HCl [pH 7.4] plus 5 mM EDTA and protease inhibitor cocktail set I and phosphatase inhibitor cocktail set I [Calbiochem]) and sonicated three times for 30 sec each. Proteins were separated by SDS-PAGE, transferred to nitrocellulose membranes, and probed with antibodies against the following proteins: phosphorylated MEK, MEK, phosphorylated Akt, Akt, phosphorylated AMPK, AMPK, p70S6K, phosphorylated p70S6K, CHOP, EPAC1 (Cell Signaling), β1 integrin, EGFR, activated EGFR, HIF-1α, (Chemicon International), PFKP (Abgent), GAPDH, GLUT3 (GeneTex), LDHA, PDHE1α, DLAT, DLD, HIF-3α, Rap1, sAC, EPAC2, OGT, Lamin A/C (Santa Cruz Biotechnology), Aldolase (Polysciences), GFPT (Protein-Tech Group), HIF-2α (Abcam), and HA-tag (Covance). After probing with HRP-conjugated secondary antibodies, blots were developed using SuperSignal West Femto chemiluminescence reagent (Pierce Biotechnology). Images were captured using Fluor Chem 8900 imager (Alpha Innotech).

Quantitative PCR

First strand cDNA pools of S1, T4-2 and reverted T4-2 cells were obtained from total RNA of each sample by using SuperScript II (Invitrogen). For each sample, reverse transcription was carried out with random hexamer and with oligo dT primer following the manufacturer's instruction, and the two reactions were mixed in a ratio of 9:1. Expression levels of EGFR, ITGB1, GLUT3 and 18S ribosomal RNA (used as a control) were quantified in LightCycler system (Roche) using QuantiTect SYBR Green PCR Kits (QIAGEN) and the reverse transcription mixtures. Expression levels of EGFR, ITGB1, GLUT3 were normalized to that of 18S ribosomal RNA.

Measurement of Rap1 Activity

Rap1 activity was measured as described previously (Itoh et al., 2007). Briefly, cell colonies were extracted from lrECM as described above, and lysed in lysis buffer (50 mM Tris-HCl [pH 7.4], 500 mM NaCl, 1% NP40, 2.5 mM MgCl2, 10% glycerol, 10 µg/ml aprotinin and 10 µg/ml leupeptin) at 4° C. for 30 min. Lysates were cleared by centrifugation at 15,000×g at 4° C. for 15 min. Supernatants (containing 300 µg protein in 300 µl) were incubated with 15 µg of GST-tagged RalGDS-RBD fusion protein immobilized on Glutathione Sepharose 4B beads (GE Healthcare), at 4° C. for 1 hr. Beads were washed trice in lysis buffer and resuspended in Laemmli buffer. Samples were separated by SDS-PAGE, followed by transfer to polyvinylidene fluoride membranes (0.2 µm pore) and immunoblotting using anti-Rap1 antibody.

Measurement of In Vitro Invasive Activity

Invasive activity was examined using BD Biocoat GFR (growth factor reduced) Matrigel invasion chamber (BD Biosciences). Before the assay, lower surface of the membrane of the upper chamber was coated with collagen type I (10 µg/ml). MDA-MB-231 cells cultured on 2D plastic for two days with H14 medium containing different concentrations of glucose (17.5, 1.75 or 0 mM) or supplemented with metabolic inhibitors (40 µM IA or 20 µM DON, with 17.5 mM glucose) were detached by trypsinization, and 25,000 cells in each condition were seeded on the upper chambers. Both upper and lower chambers were filled with medium of the same formulations as that in each 2D culture. After 16 hours, cells were fixed with 4% PFA in PBS and stained with crystal violet.

Examples

Increased Glucose Metabolism Activates Pathways Involved in Oncogenesis

To test whether increased glucose metabolism itself is required for oncogenic signaling events, we utilized 3D lrECM cultures of HMT-3522, a breast cancer progression series which includes non-malignant (S1) and malignant (T4-2) human breast epithelial cells from the same individual (Briand et al., 1987; Petersen et al., 1992; Rizki et al., 2008). Using these cells, we have described the involvement and reciprocity of multiple signaling pathways including EGFR, β1 integrin, PI3K-Akt and MEK-ERK in oncogenic events (Beliveau et al., 2010; Bissell et al., 2005). Suppressing activated oncogenic signal in any one of these pathways would adjust all the others, and the cancer cells recover their ability to perceive microenvironmental cues that lead to the formation of growth-arrested, basally polarized acinus-like structures as seen in primary non-malignant cells (FIGS. 2A and 3A; Beliveau et al., 2010; Itoh et al., 2007; Kenny and Bissell, 2007; Liu et al., 2004; Wang et al., 2002; Wang et al., 1998; Weaver et al., 2002; Weaver et al., 1997). We thus used this "phenotypic reversion" of the cancer cells as an assay to examine how the signaling integration plan of the breast acini could involve glucose metabolism.

Figure 2A:
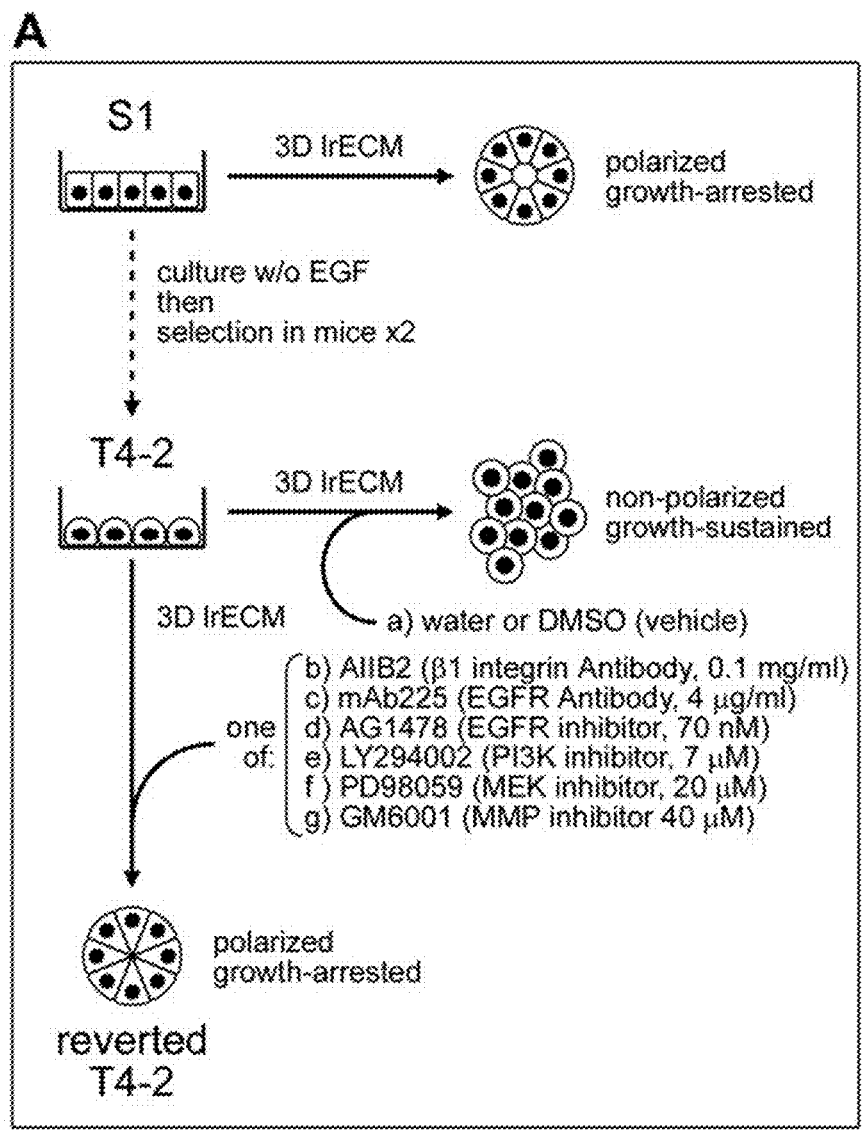
FIG. 2A, FIG. 2B, 2C, 2D, 2E, FIG. 2F, 2G, 2H, 2I, 2J, FIG. 2K and FIG. 2L, 2M, 2N 2O is a series of images and graphs showing that glucose metabolism is an integral part of the oncogenic signaling pathway.
Figures 2B, 2C, 2D, 2E:
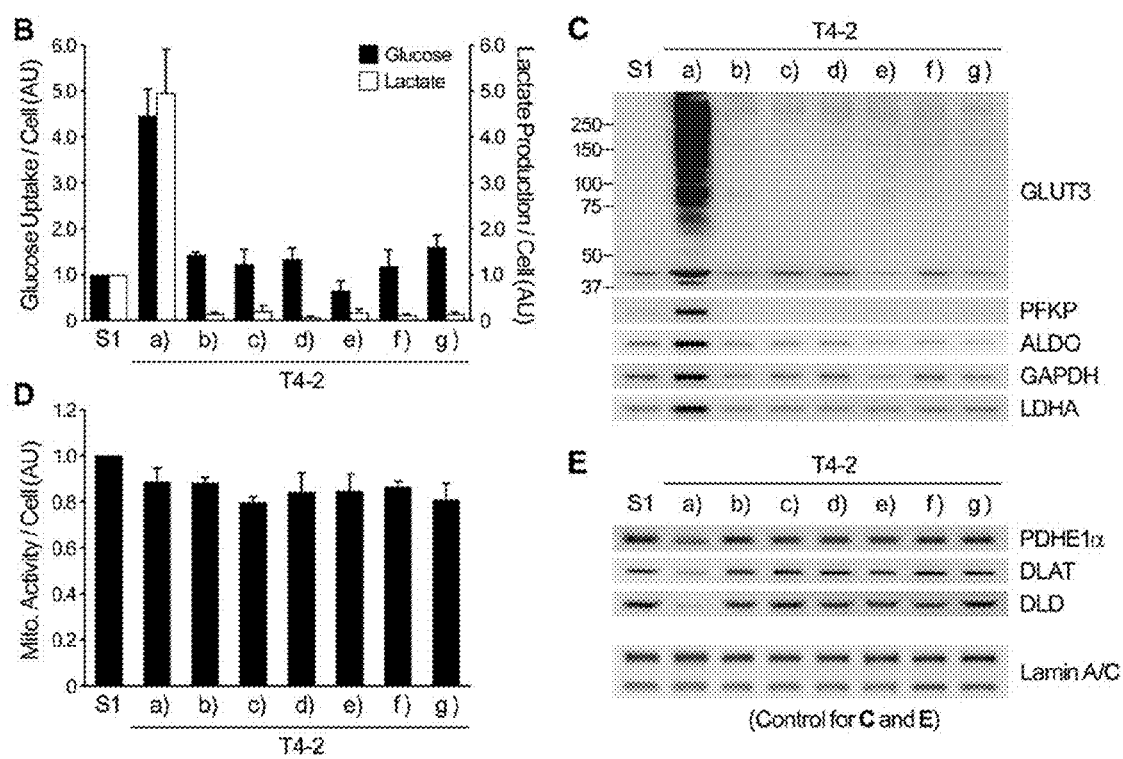

We compared glucose uptake and lactate production, markers of aerobic glycolysis in cancer, in malignant T4-2—with those in non-malignant S1—cells or with phenotypically-reverted T4-2 cells cultured in 3D lrECM. FIG. 2A shows a diagrammatic scheme of 3D lrECM (laminin-rich extracellular matrix) gel cultures of S1, T4-2 and reverted T4-2 cells. FIGS. 2B and 2C show glucose uptake (black bars, FIG. 2B), lactate production (white bars, FIG. 2B) and Western blots of proteins related to these functions (FIG. 2C) in conditions indicated in FIG. 2A. (AU=arbitrary units.) Results are mean±SEM of at least 3 independent experiments for this and all other figures. Both glucose uptake and lactate production were significantly higher in T4-2 than in S1 cells. But these parameters became as low as—or even lower than—S1 cells in the reverted T4-2 cells regardless of the inhibitors used to revert (FIGS. 2A and 2B).

Figures 3A, 3B, 3C:
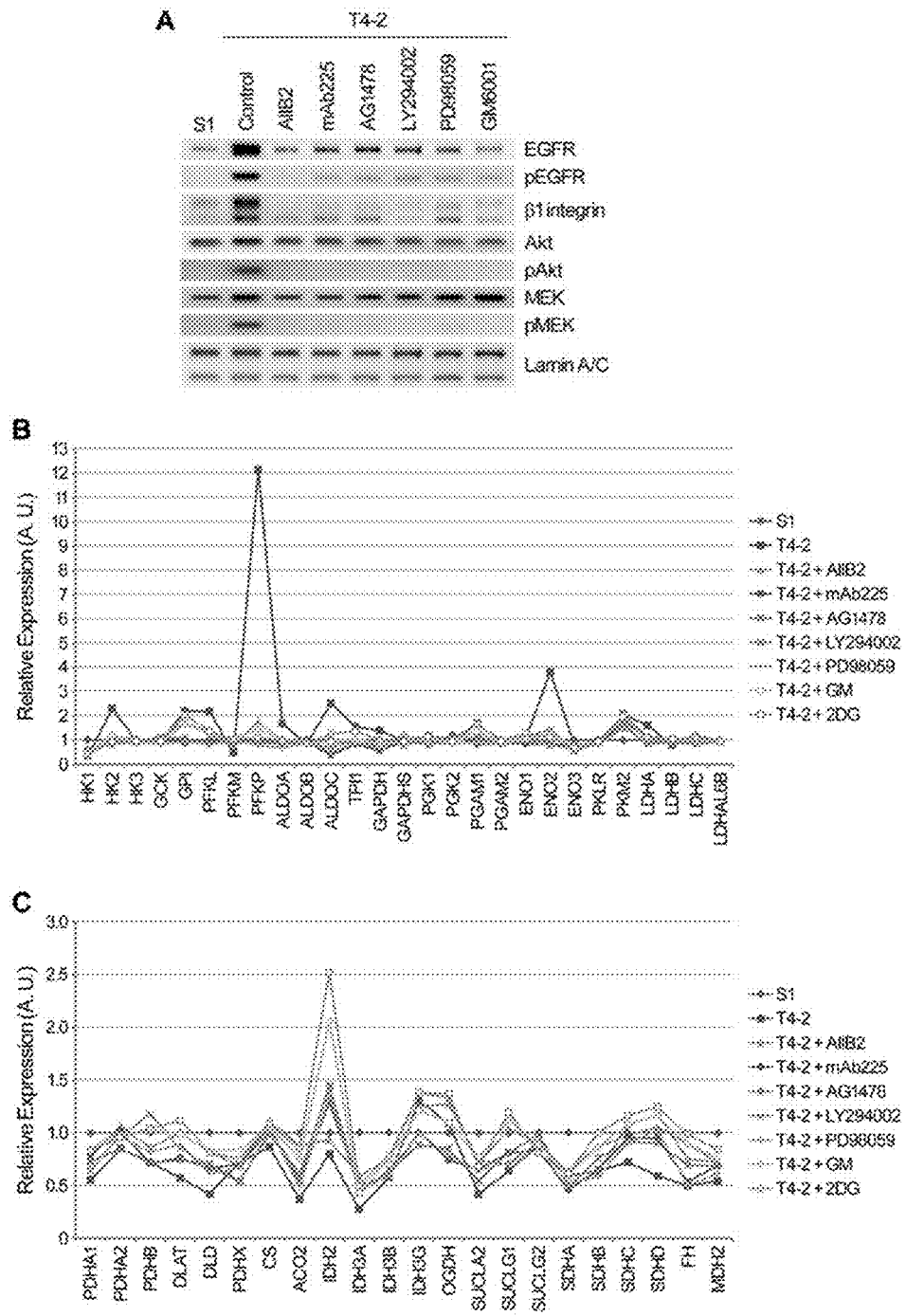
FIG. 3A, 3B, 3C is a Western blot image and a pair of graphs showing gene expression profiling of S1, T4-2 and phenotypically reverted T4-2 cells.

We examined gene expression profiles of these cells using both our own previously published and unpublished data, and showed that most of the glycolytic enzymes in T4-2 cells were higher than in S1 but that the alterations could be reversed in reverted T4-2 cells (FIG. 3B). FIG. 3A shows Western blots of signaling intermediates in 3D lr-ECM cultures of S1, T4-2 and T4-2 cells reverted by different signaling inhibitors (Related to FIG. 1A). FIGS. 3B and 3C shows the expression of genes involved in glycolysis (FIG. 3B) and citric acid cycle (FIG. 3C) under conditions shown in FIG. 3A. Results were retrieved from microarray analyses and shown as relative expression (arbitrary units) compared to S1 cells.

We confirmed changes in protein levels of the enzymes by Western blots: platelet-type phosphofructokinase (PFKP), glyceraldehyde-3-phosphate dehydrogenase (GAPDH), aldolase (ALDO) and lactate dehydrogenese A (LDHA) were all up-regulated in T4-2 cells (FIG. 2C; hereinafter, see FIG. 1 for reminder of the pathways examined). GLUT3, a facilitative glucose transporter, showed the most dramatic up-regulation in T4-2 cells (>100 fold; FIG. 2C), whereas GLUT1, another glucose transporter known to go up in a number of other tumor types (Godoy et al., 2006), was unaltered (data not shown).

FIGS. 2D and 2E show mitochondrial oxidation (FIG. 2D) and western blots of pyruvate dehydrogenese complex (PDC) components (FIG. 2E) in conditions indicated in FIG. 2A. Note that laminin A/C is a control for both FIG. 2C and FIG. 2E. Unlike the glycolytic intermediates, mitochondrial activity (oxidation) was essentially unchanged under all reverting conditions (FIG. 2D). But the expression of the components of pyruvate dehydrogenase complex (PDC), which mediates entry of pyruvate into citric acid cycle, was higher in S1 and reverted T4-2 than in T4-2 cells (FIG. 2E), providing a possible explanation for the stable mitochondrial activity despite the significant difference in glucose uptake. Thus mitochondrial metabolism need not be necessarily impaired when glucose uptake and metabolism is highly increased (also see data for normal and RSV-transformed chick fibroblasts, Bissell et al., 1976).

We reasoned that if the metabolic changes observed were equal partners of the other oncogenic pathways in the reversion model, then direct inhibition of glucose metabolism in T4-2 cells should suppress the malignant phenotype. This was indeed the case as inhibition of glucose metabolism using 2-deoxy-D-glucose (2DG) induced phenotypic reversion including growth arrest (FIGS. 2F and 2G), re-establishment of basally polarized acini (FIGS. 2F and 2H) and a decrease in the levels and/or activities of EGFR, β1 integrin, Akt and MEK as well as dramatic down-regulation of GLUT3 and the glycolytic enzymes (FIG. 2K).

Figures 2F, 2G, 2H, 2I, 2J:
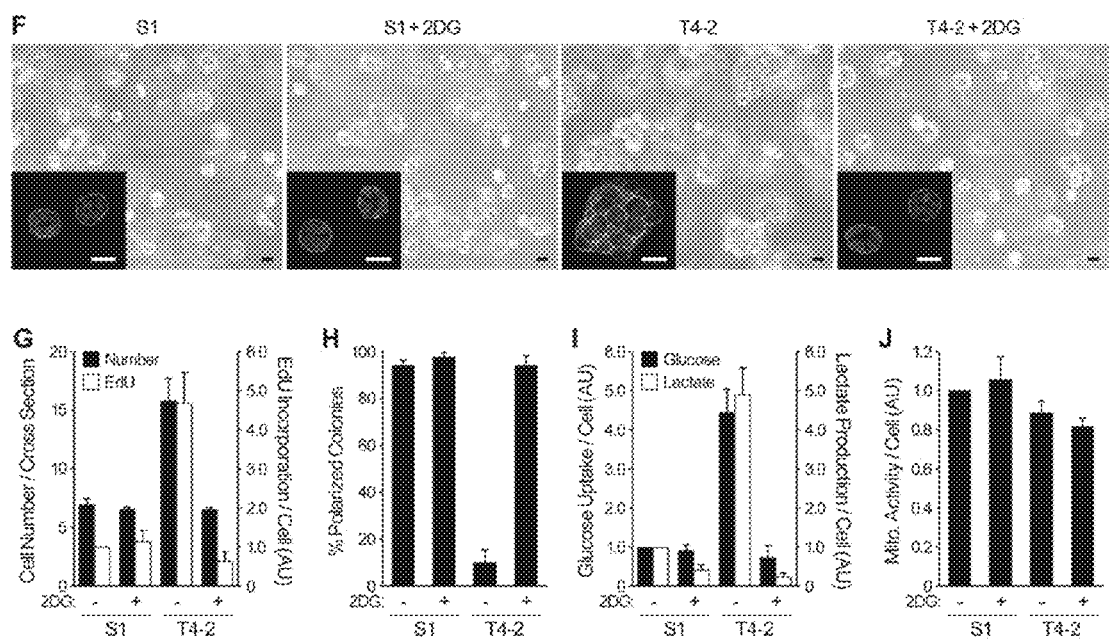

FIG. 2F shows phase contrast and confocal immunofluorescence (IF, inset) images of S1 and T4-2 cells cultured in 3D lrECM with or without 2-deoxy-D-glucose (2DG, 4 mM). α6 integrin, DAPI-staining of nuclei. Bars, 20 µm. Also shown in FIGS. 2G-J are cell numbers at the colony mid-section (black bars, FIG. 2G), EdU incorporation per cell (white bars, FIG. 2G), percent colonies with basal polarity (FIG. 2H), glucose uptake (black bars, FIG. 2I), lactate production (white bars, FIG. 2I) and mitochondrial oxidation (FIG. 2J) in conditions shown in FIG. 2F. FIG. 2K shows Western blots of signaling intermediates, GLUT3, metabolic enzymes and other proteins related to, or influenced by, glucose metabolism in conditions shown in FIG. 2F. Again mitochondrial activity was essentially unaffected (FIG. 2J) but PDC components were elevated (FIG. 2K). Importantly, treatment of S1 cells with the same level of 2DG altered neither the acinar morphology nor the growth rate (FIGS. 2F-2H). These data demonstrate that increased glucose uptake and metabolism are essential for maintenance of the malignant phenotype.

To determine the pathways that allow increased glucose uptake to translate into oncogenic signaling, we examined the activity of AMP-activated protein kinase (AMPK) and mammalian target of Rapamycin (mTOR) pathways known to be involved in intracellular fuel and energy status (Marshall, 2006). Treatment with 2DG in the 3D cultures did not affect phosphorylation of AMPK or S6K, major targets of mTOR complex1 (Shackelford and Shaw, 2009), indicating that these two pathways are not significantly influenced by inhibition of glucose metabolism in 3D (FIG. 2K). The mTOR inhibitor, rapamycin, partially reduced Akt activity and cellular proliferation but did not induce phenotypic reversion (FIGS. 2L-2O). FIG. 2L shows confocal IF images of 3D cultures of T4-2 cells treated with Rapamycin (Rapa, 0.01-1.0 µM). α6 integrin, nuclei. Bars, 20 µm. FIGS. 2M and 2N show cell numbers at the colony mid-section (FIG. 2M) and percent colonies with basal polarity (FIG. 2N) in conditions shown in FIG. 2L. FIG. 2O shows Western blots of signaling intermediates in conditions shown in FIG. 2L.

Figure 2K:
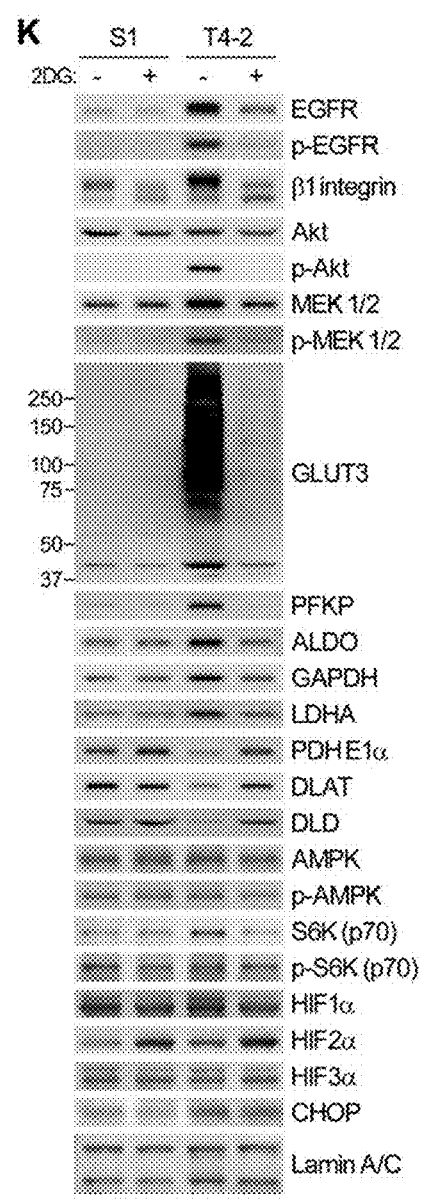
Figures 2L, 2M, 2N, 2O:
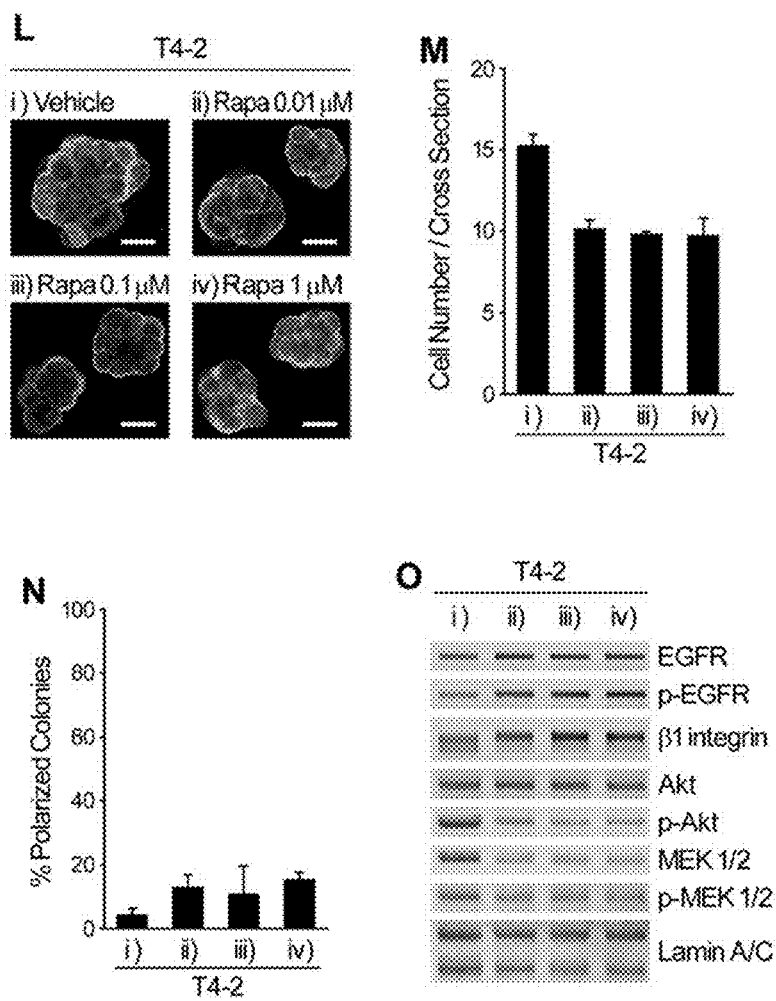

Similarly, the levels of hypoxia-inducible factor (HIF) 1α, a well-known regulator of glycolytic enzymes and glucose transporters (Kroemer and Pouyssegur, 2008) as well as HIF-2- and 3-α did not correlate with the malignant phenotype or the level of expression of glycolytic enzymes and GLUT3 (FIG. 2K). Finally, expression of an ER stress marker, CHOP (C/EBP homologous protein), was unchanged by the 2DG treatment (FIG. 2K). Thus feedback of glucose metabolism to signaling pathways need not involve known fuel, energy and stress sensors.

Glucose Uptake is a Critical Step in Determining the Malignant/Non-Malignant Phenotypes in 3D-lrECM To examine to what extent and how the oncogenic signaling activation and the malignant phenotype were dependent on the level of glucose uptake and metabolism, we knocked down GLUT3 by siRNA in T4-2 cells using modified 3D lrECM cultures (3D-on top [3D-OT] cultures; see Experimental Procedures) supplemented with medium containing 4 different concentrations of glucose ranging from 0 mM to 17.5 mM (concentration of glucose in the medium used to culture the HMT-3522 progression series [Briand et al., 1987]).

In T4-2 cells treated with non-targeting negative control siRNA, reducing glucose from 17.5 mM to 5.5 mM (physiological glucose level) produced no significant differences in growth, morphology or the levels of signaling intermediates (FIG. 4A-4D). In 1.75 mM glucose, basal polarity was re-established and the growth rate, the expression of β1 integrin and the activity of Akt were reduced. Reducing glucose to 0 mM further led to more appreciable growth arrest, reduction in EGFR and MEK and formation of polarized acinus-like structures with even lower oncogenic signaling activities (FIG. 4A-4D). Knockdown of GLUT3 sensitized T4-2 cells more significantly to the reduction in glucose level (FIG. 4A-4D), suggesting that increased uptake mediated by high expression of the glucose transporter is for maintaining the malignant phenotype.

We also confirmed the effects of reducing glucose in the conventional 3D lrECM cultures where cells are placed inside the gels without GLUT3 knockdown. In T4-2 cells cultured with no or reduced glucose, expression of both the glycolytic enzymes and GLUT3 shifted towards the levels in S1 cells. The PDC components showed the opposite trend as expected (FIG. 6D). As was the case in 2DG-treated cells, even a 100 fold change in glucose concentration did not alter the rate of growth, acinar organization or the pattern of signaling intermediates in nonmalignant S1 cells in 3DlrECM (FIGS. 6A-6D).

Malignancy is the end result of many changes in the genome as well as dramatic imbalance in gene expression over decades. Nevertheless to directly assess the oncogenic potential of increase in glucose uptake we ventured whether increase in GLUT3 in nonmalignant but immortal cells could interfere with integration of signaling pathways and lead to disorganization of acinar structures. We infected nonmalignant S1 cells with either empty or GLUT3-encoding lentivirus and then placed them in 3D lrECM. Intriguingly, when cells were cultured with 5.5 mM or higher glucose concentration, over-expression of GLUT3 by itself was sufficient to give rise to disorganized colonies (FIGS. 4E and 4F).

Figures 4A, 4B, 4C:
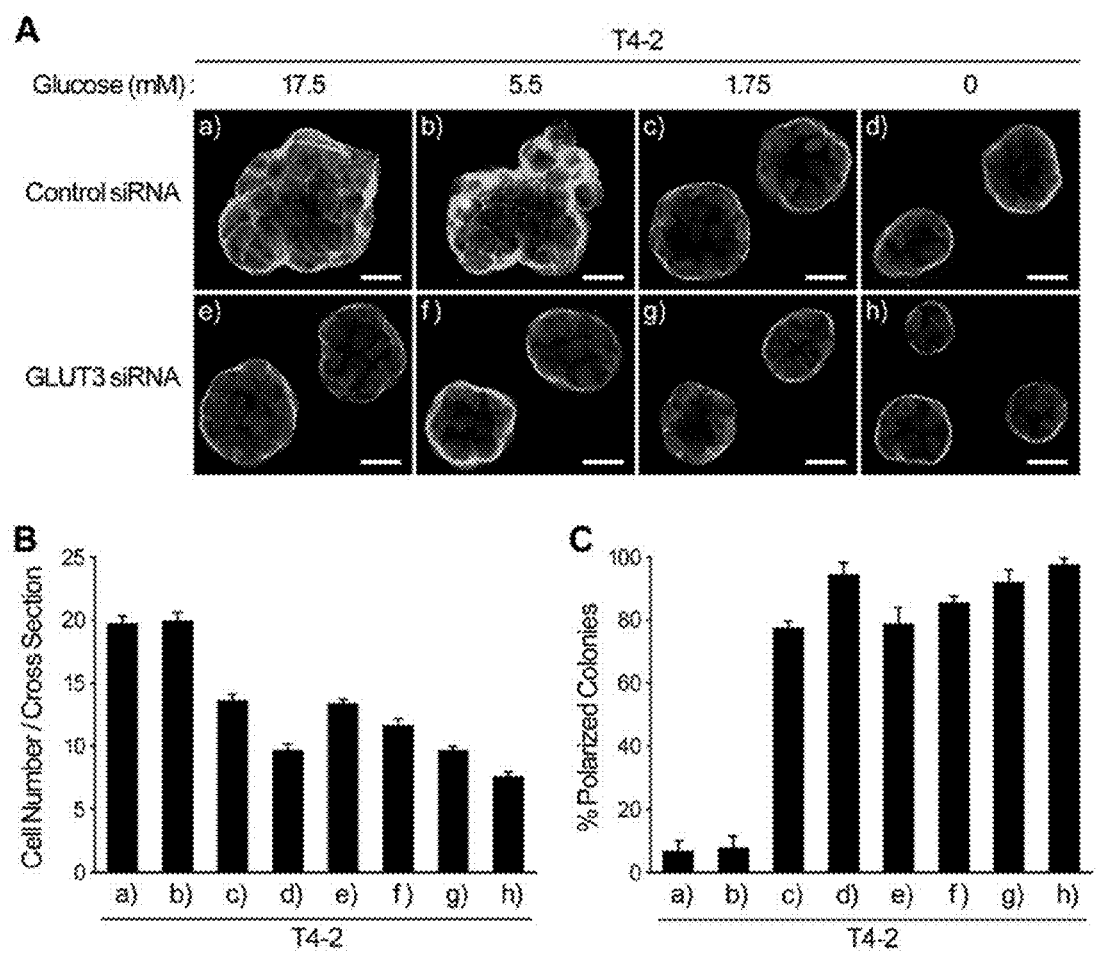
FIG. 4A, 4B, 4C, FIG. 4D, FIG. 4E, 4F and FIG. 4G is a series of images and graphs showing that glucose uptake and metabolism determine the signaling activity and the morphology of malignant and non-malignant mammary epithelial cells.
Figure 4D:
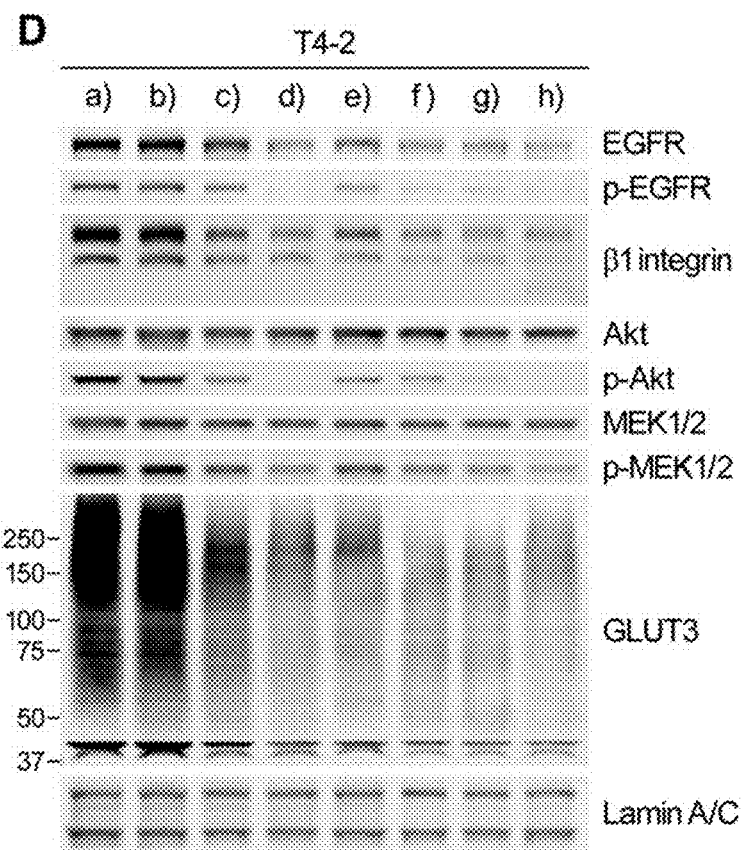
Figures 4E, 4F:
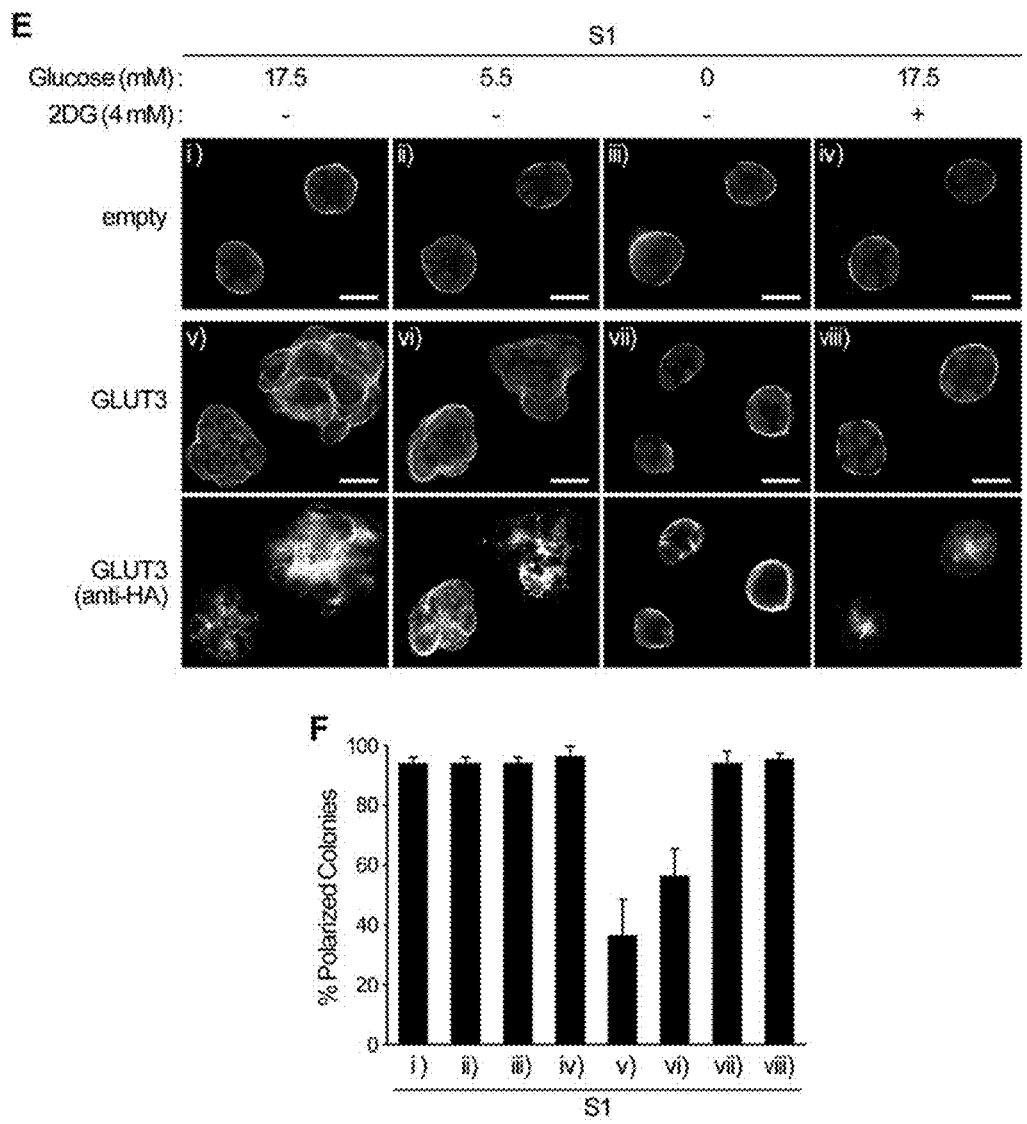
Figure 4G:
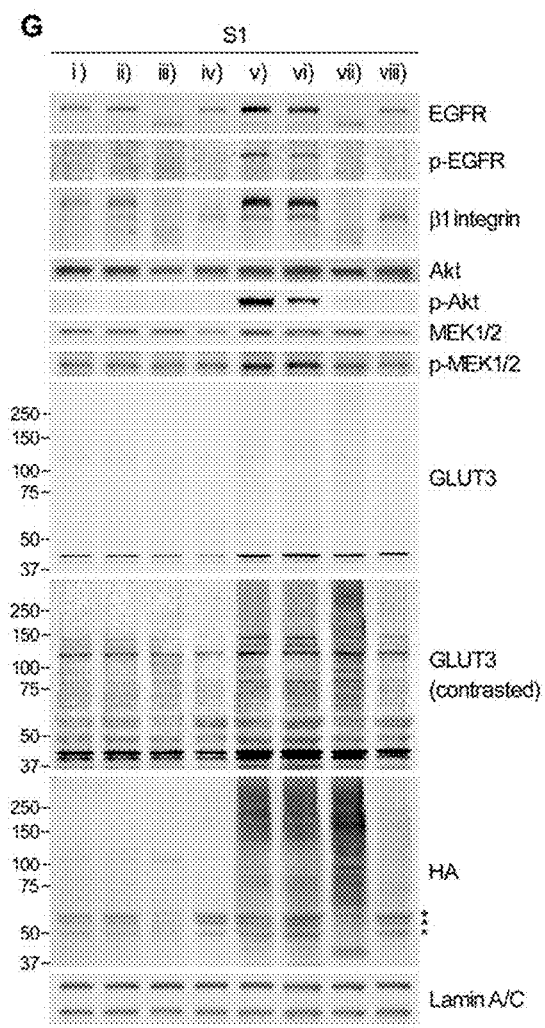

FIG. 4E shows confocal IF images of S1 cells infected with empty or GLUT3-HA-encoding lentivirus, cultured in 3D lrECM with 2DG (4 mM) or different concentration of glucose. α6 integrin, nuclei. Immuno-staining with anti-HA antibody is shown in gray scale. Bars, 20 µm. FIG. 4F shows the percent colonies with basal polarity in conditions shown in FIG. 4E. FIG. 4G shows Western blots of signaling intermediates, GLUT3 and HA epitope in conditions shown in FIG. 4E. Asterisks indicate non-specific bands. Western analysis showed that increase in GLUT3 9 expression led to over-expression and/or activity of the key signaling intermediates involved in oncogenic events (FIG. 4G). As was the case with malignant T4-2 cells, the phenotype could be reversed when glucose metabolism was inhibited either by removal of glucose or by addition of 2DG (FIGS. 4E-4G). The Glycolytic Metabolism Between GAPDH and LDH Potentiates Malignant Phenotype Through Upregulation of β1 Integrin To understand how changes in glucose uptake translated into the dramatic alteration of the signaling pathways, we utilized iodoacetate (IA) and oxamate (OX), inhibitors of GAPDH and LDH, the expression of which are increased in T4-2 cells (FIG. 2A-2K). OX is presumed to inhibit GAPDH as well since it blocks the supply of NAD+, a coenzyme for GAPDH (see the scheme in FIG. 1).

Extracellular glucose is taken up by glucose transporters including GLUT3 as well as by diffusion, and is metabolized by hexokinase (HK) and glucose phosphate isomerase (GPI) to enter different metabolic pathways. Glycolytic pathway includes subsequent steps mediated by PFK, ALDO and GAPDH; LDH also supports glycolytic pathway by production of GAPDH coenzyme NAD+. These enzymes are all up-regulated in T4-2 cells leading to loss of integration of form and function. sAC-EPAC-Rap1 pathway, regulates β1 integrin positively, most probably through regulation of ATP production in glycolytic pathway. HBP is rate-limited by GFPT, which is also up-regulated through activation of oncogenic signaling. The downstream O-GlcNAcylation of target proteins mediated by OGT (O-linked-N-acetylglucosaminyl transferase) regulates the expression of β1 integrin, EGFR and GLUT3. Inhibition of any one of the key metabolic enzymes or the key signaling molecules results in suppression of all the others, re-establishment of the polarized acinar structure and growth arrest.

Factors involved in the scheme of FIG. 1 are indicated as follows: italic, metabolites; bold, proteins; and bold italic, genes. GLUT3, EGFR, αXβ1, PFK, GFPT, ALDO, GAPDH, LDH, proteins up-regulated in T4-2 cells; ATP, NADH, NAD$^+$, energy carrier molecules; 2DG, SDG-P, BADGP, AZS/DON, IA, KH7, OX, chemical reagents which do induce phenotypic reversion; and TM, OGM, chemical reagents which do not induce phenotypic reversion.

FIG. 1 further shows GLUT3, PFKP, GAPDH, ALDOC, LDHA and GFPT in a pathway where glucose is taken up by GLUT3, PFK acts on F6P→F1,6BP; GAPDH acts on GAD3P→1,3BPG; ALDO acts on F1,6BP→GAD3P, LDH acts on pyruvate→lactate, and GFPT acts on F6P→UDP-GLCNAc. The interrelationship of the glycolytic pathway with the cell signaling from EGFR and alphax-beta 1 integrin cell surface molecules is shown.

Figures 5A, 5B, 5C, 5D, 5E, 5F:
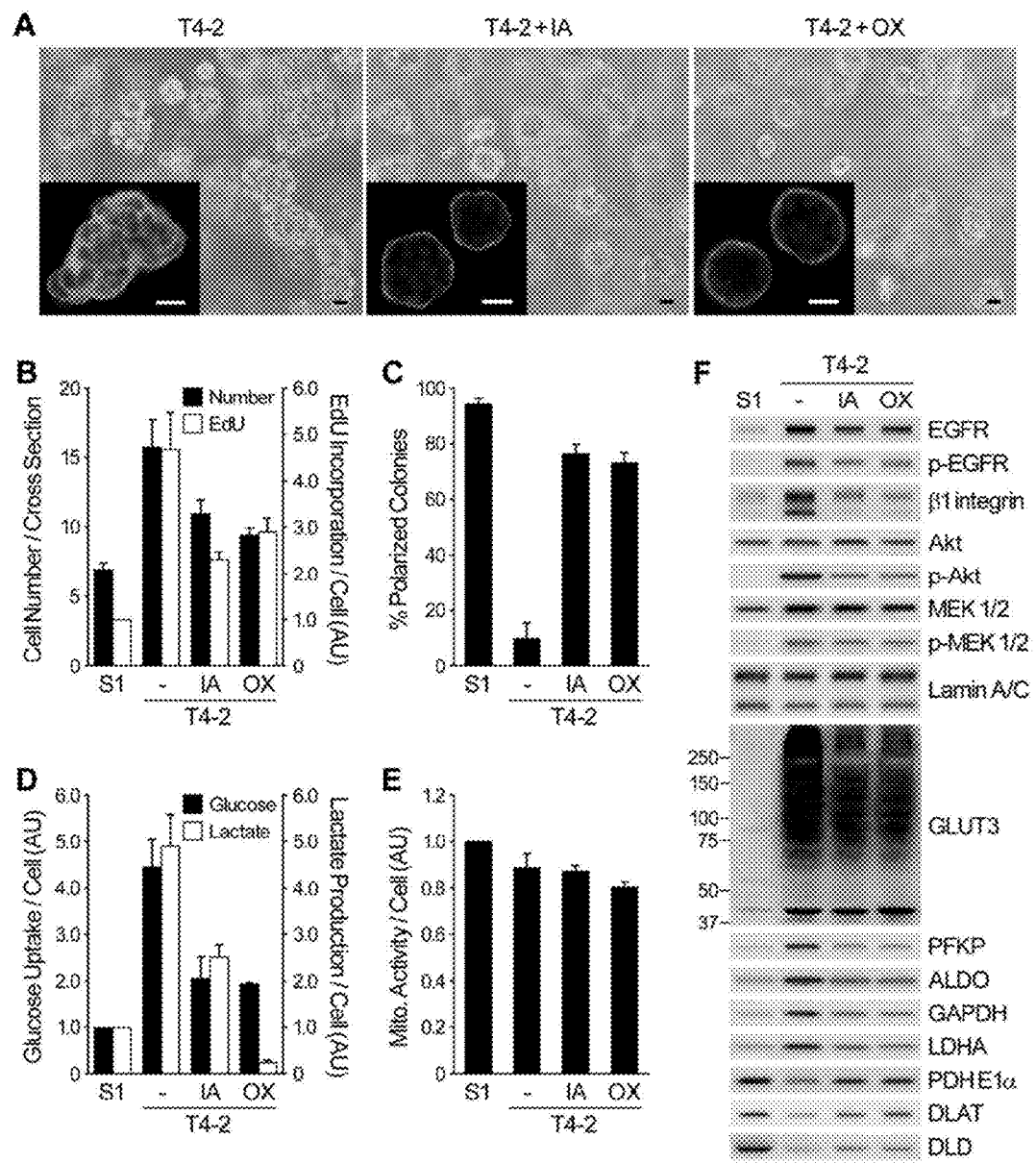
FIG. 5A, 5B, 5C, 5D, 5E, 5F and FIG. 5G, 5H, 5I, 5J is a series of images and graphs showing inhibition of glycolytic pathway reduces oncogenic signaling and reverses the malignant phenotype.

When T4-2 cells were treated with either inhibitors in basal medium (17.5 mM glucose), they formed organized colonies (FIGS. 5A and 5C) but the rate of proliferation remained higher than in S1 acini (FIGS. 5A and 5B). Expression of β1 integrin and Akt activity were reduced appreciably, whereas EGFR and MEK were affected only slightly (FIG. 5F). These characteristics are nearly identical to those of the T4-2 cells cultured with 1.75 mM glucose (see FIG. 6A-6D). Under these conditions, glucose uptake, lactate production and expression of glycolytic enzymes and GLUT3 were partially but clearly suppressed. The expression of PDC components was partially restored, whereas again the mitochondrial activity was not appreciably affected by the inhibitors (FIGS. 5D-5E).

FIG. 5A shows phase contrast and IF (inset) images of T4-2 cells cultured in 3D with or without iodoacetate (IA, 20 μM) or oxamate (OX, 50 mM). α6 integrin, nuclei. Bars, 20 μm. FIGS. 5B-E show cell numbers at the colony mid-section (black bars, FIG. 5B), EdU incorporation per cell (white bars, FIG. 5B), percent colonies with basal polarity (FIG. 5C), glucose uptake (black bars, FIG. 5D), lactate production (white bars, FIG. 5D) and mitochondrial oxidation (FIG. 5E) in conditions shown in FIG. 5A.

Figure 6A:
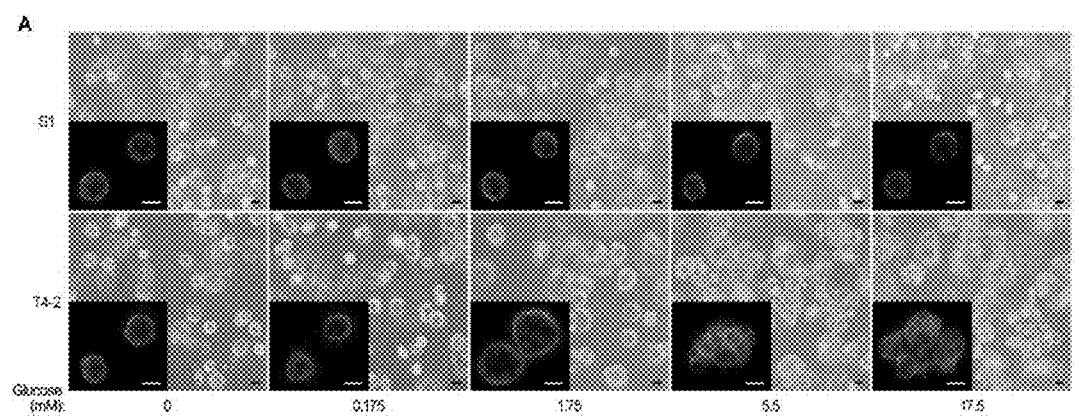
FIG. 6A and FIG. 6B, 6C, 6D is a series of images and graphs showing that the glucose concentration determines the phenotype, the level of oncogenic signaling and the patterns of glycolytic intermediates in T4-2 cancer cells.
Figures 6B, 6C, 6D:
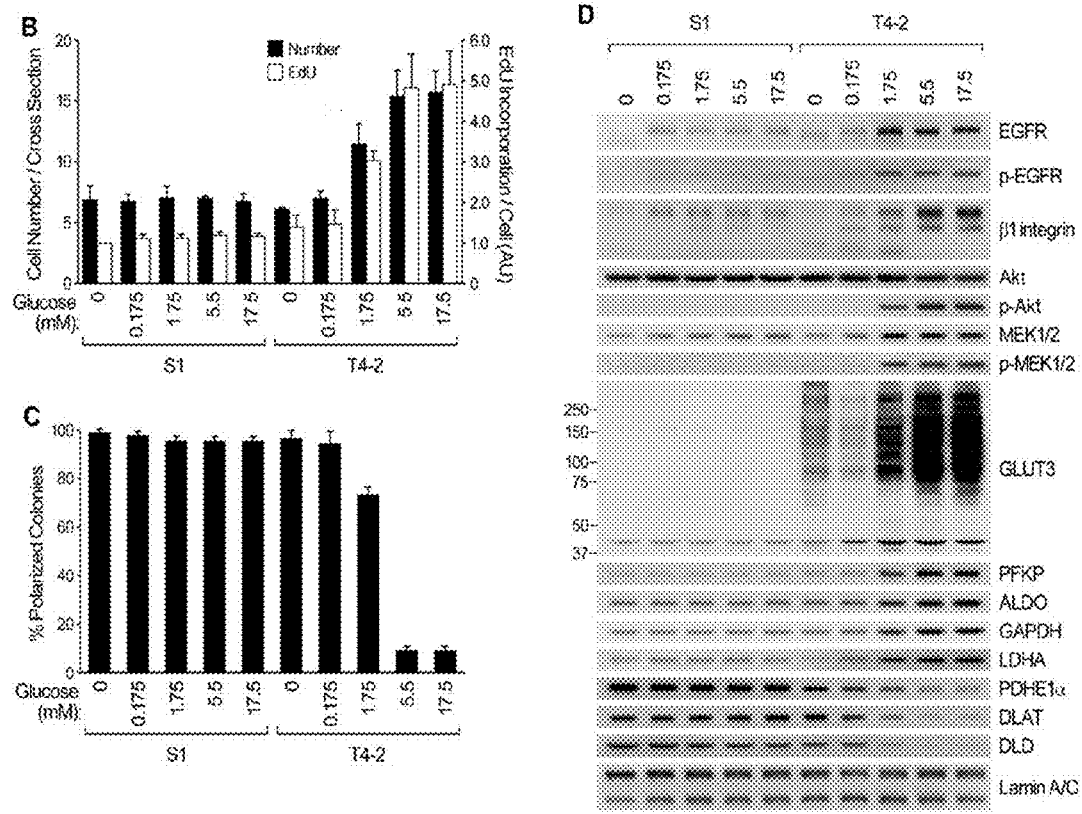

FIG. 6A shows phase contrast and confocal IF (inset) images of 3D cultures of S1 and T4-2 cells in different glucose concentrations. Stained are α6 integrin and nuclei, shown as lighter in contrast. Bars, 20 μm. FIGS. 6B and 6C show cell numbers at the colony mid-section (black bars, FIG. 6B), EdU incorporation per cell (white bars, FIG. 6B) and percent colonies with basal polarity (FIG. 6C) in conditions shown in FIG. 6A. FIG. 6D shows Western blots of signaling intermediates, GLUT3 and metabolic enzyme in conditions shown in FIG. 6A.

Figures 5G, 5H, 5I, 5J:
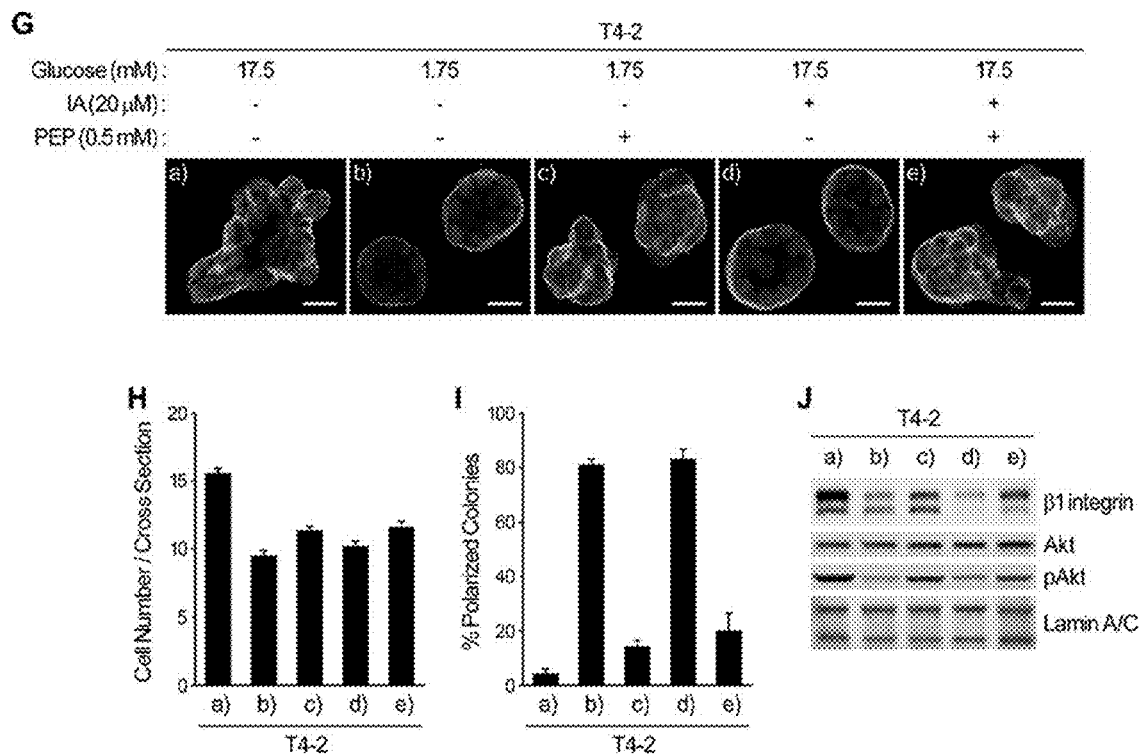

Knockdown of GAPDH by siRNA essentially reproduced the above results (FIGS. 7A-7D). Supplementation of phosphoenolpyruvate (PEP), an intermediate metabolite in the pathway between GAPDH and LDH (see FIG. 1), to IA-treated or glucose-deprived (1.75 mM) T4-2 cells partially recovered β1 integrin expression and Akt activity and reproduced the disorganized structure (FIGS. 5G-5J) further validating that the metabolic reactions between GAPDH and LDH are involved in malignant progression. FIG. 5F shows Western blots of signaling intermediates, GLUT3 and metabolic enzymes in conditions shown in FIG. 5A. FIG. 5G shows confocal IF images of T4-2 cells cultured in 3D lrECM with low glucose (1.75 mM) or IA (20 μM), with or without phosphoenolpyruvate (PEP, 0.5 mM). α6 integrin, nuclei. Bars, 20 μm. FIGS. 5H and 5I shows cell numbers at the colony mid-section (FIG. 5H) and percent colonies with basal polarity (FIG. 5I) in conditions shown in FIG. 5G. FIG. 5J shows protein expression and/or activation of β1 integrin and Akt in conditions shown in FIG. 5G.

Figures 7A, 7B, 7C, 7D:
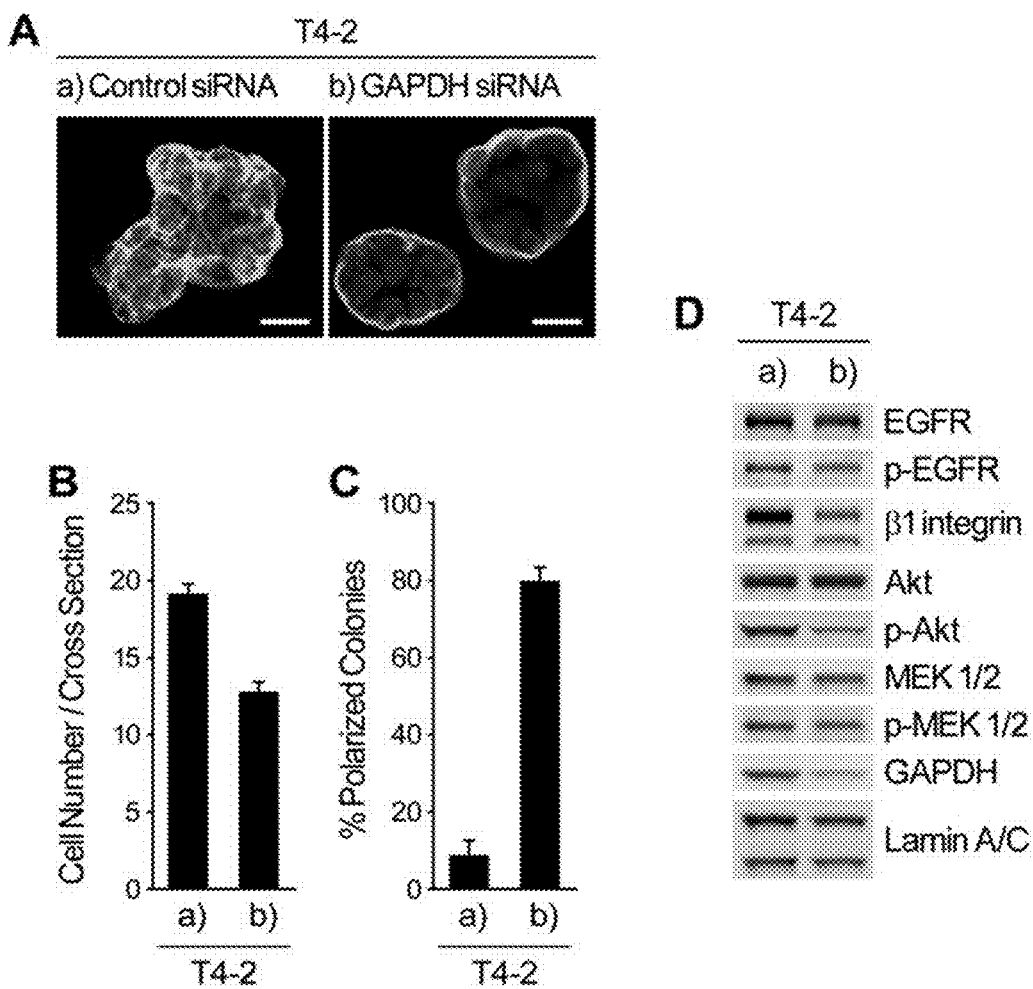
FIG. 7A, 7B, 7C, 7D, FIG. 7E, 7F, 7G, 7H, and FIG. 7I, 7J, 7K is a series of images and graphs showing that the decrease in pyruvate metabolism or inhibition of mitochondrial ATP synthesis is not responsible for the phenotypic reversion induced by inhibition of glucose metabolism.
Figures 7E, 7F, 7G, 7H:
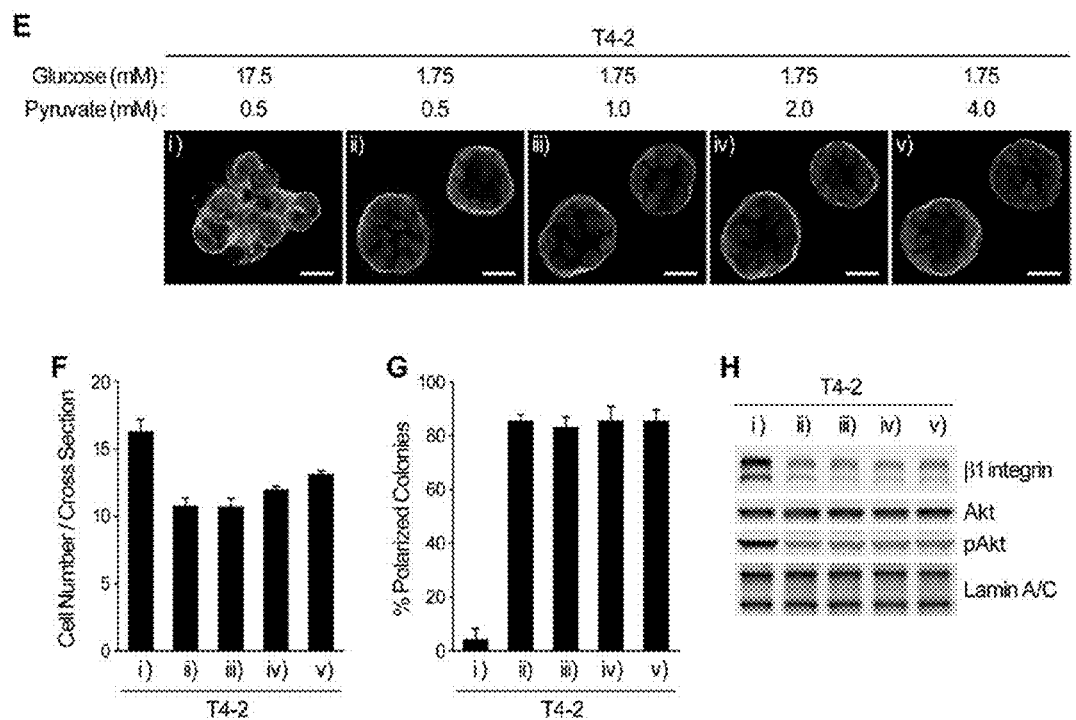

However, supplementation of pyruvate, the result of conversion from PEP by pyruvate kinase, did not rescue the malignant phenotype (FIG. 7E-7H), suggesting that the conversion step itself is necessary. FIG. 7A shows confocal IF images of T4-2 cells transfected with control or GAPDH siRNA, cultured in 3D-on top (OT) lrECM. Stained are α6 integrin and nuclei, shown as lighter in contrast. Bars, 20 μm. FIGS. 7B and 7C show cell numbers at the colony mid-section (FIG. 7B) and percent colonies with basal polarity (FIG. 7C) in conditions shown in FIG. 7A. FIG. 7D shows Western blots of signaling intermediates in conditions shown in FIG. 7A. FIG. 7E shows confocal IF images of T4-2 cells cultured in 3D lrECM with different concentrations of glucose and pyruvate. Stained are α6 integrin and nuclei, shown as lighter in contrast. Bars, 20 μm. FIGS. 7F and 7G show cell numbers at the colony mid-section (FIG. 7F) and percent colonies with basal polarity (FIG. 7G) in conditions shown in FIG. 7E. FIG. 7H shows protein expression and/or activation of β1 integrin and Akt in conditions shown in FIG. 7E.

Figures 7I, 7J, 7K:
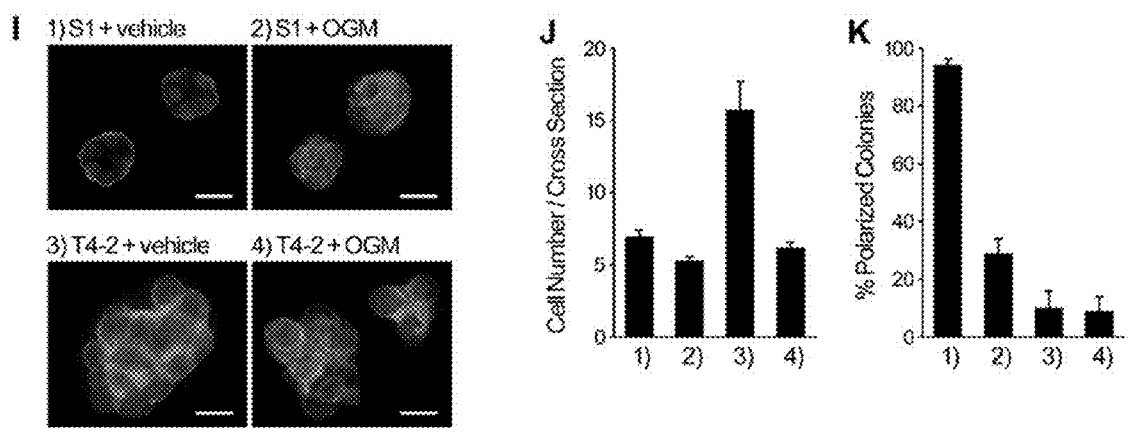

It is important to note that formation of the polarized structures is not simply due to suppression of proliferation: Treatment with oligomycin (OGM), an inhibitor of mitochondrial ATP synthase (see also FIG. 1), did not induce organized structures in T4-2 cells, despite suppressing proliferation significantly (FIG. 7I-7K). FIG. 7I shows confocal IF images of S1 and T4-2 cells cultured with Oligomycin (OGM, 4 ng/ml). Stained are α6 integrin and nuclei, shown as lighter in contrast. Bars, 20 μm. FIGS. 7J and 7K show cell numbers at the colony mid-section (FIG. 7J) and percentages of the colonies with basal polarity (FIG. 7K) in the cells from (FIG. 7I). Interestingly, S1 cells treated with OGM lost basal tissue polarity (FIG. 7I-7K). These findings suggest that inhibition of glycolytic metabolism, rather than mitochondrial ATP synthesis, is responsible for re-establishment of tissue polarity.

Rap1 Activation by Increased Glycolytic Metabolism Via EPAC Regulates β1 Integrin Signaling The phenotypes of T4-2 cells cultured with 1.75 mM glucose (FIG. 6A-D) or treated with glycolytic inhibitors (FIG. 5A-5J) are highly similar to that of T4-2 cells expressing Rap1-S17N, a dominant negative mutant of a small GTPase Rap1 (Itoh et al., 2007): Under all three conditions, basal polarity was re-established but proliferation and the key signaling pathways were not completely suppressed. Indeed, treatment with IA or growth in 1.75 mM glucose led to down-regulation of Rap1 activity without a change in its total protein level (FIG. 8A). Rescue of the malignant phenotype by PEP supplementation (FIG. 5A-5J) is also associated with Rap1 reactivation (FIG. 8A).

FIG. 8A shows Rap1 activity of T4-2 cells cultured in 3D lrECM with low glucose (1.75 mM) or IA (20 μM), with or without PEP (0.5 mM). FIG. 8B shows confocal IF images of T4-2 cells cultured in 3D-OT lrECM after transfection with the indicated siRNAs. Stained are α6 integrin and nuclei, shown as lighter in contrast. Bars, 20 μm. FIGS. 8C and 8D show cell numbers at the colony mid-section (FIG. 8C) and percent colonies with basal polarity (FIG. 8D) in conditions shown in FIG. 8B. FIG. 8E show protein expression and/or activation of β1 integrin, Akt and Rap1 in conditions shown in FIG. 8B.

Published data suggested previously that among several exchange factors for Rap1, it is EPAC (the exchange protein directly activated by cAMP) which is preferentially inhibited by Rap1 S17N (Dupuy et al., 2005). We postulated that the phenotypic reversion by inhibition of glycolytic pathway may involve suppression of EPAC-mediated Rap1 activation. Knockdown of both EPAC-1 and -2 in T4-2 cells reduced Rap1 activity and led to partially-reverted phenotype analogous to IA treatment or cultivation in 1.75 mM glucose (FIGS. 8B-8E).

Figures 8F, 8G, 8H, 8I:
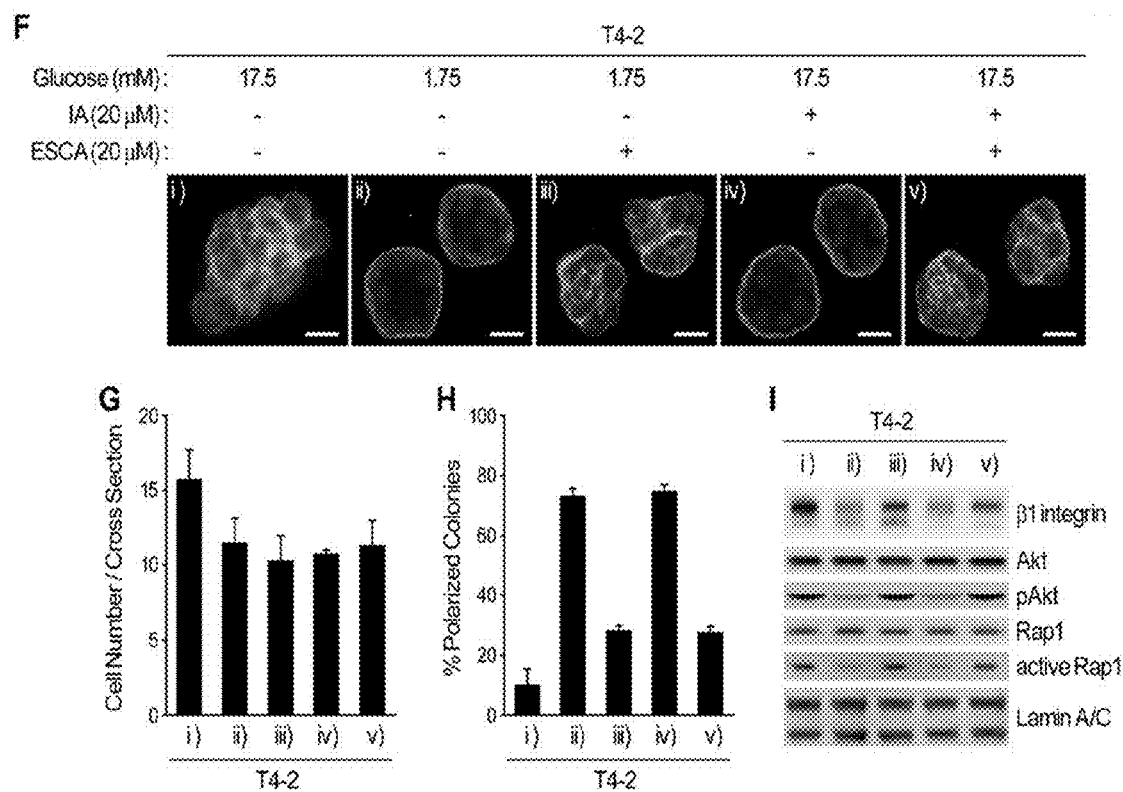
Figure 8J:
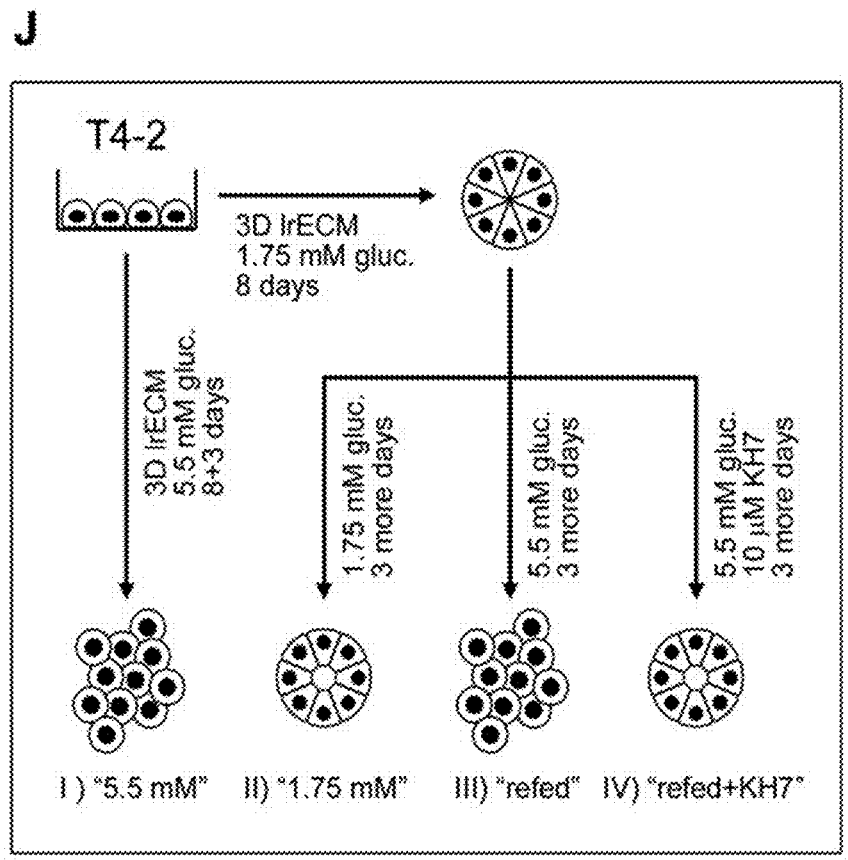
Figures 8K, 8L, 8M, 8N:
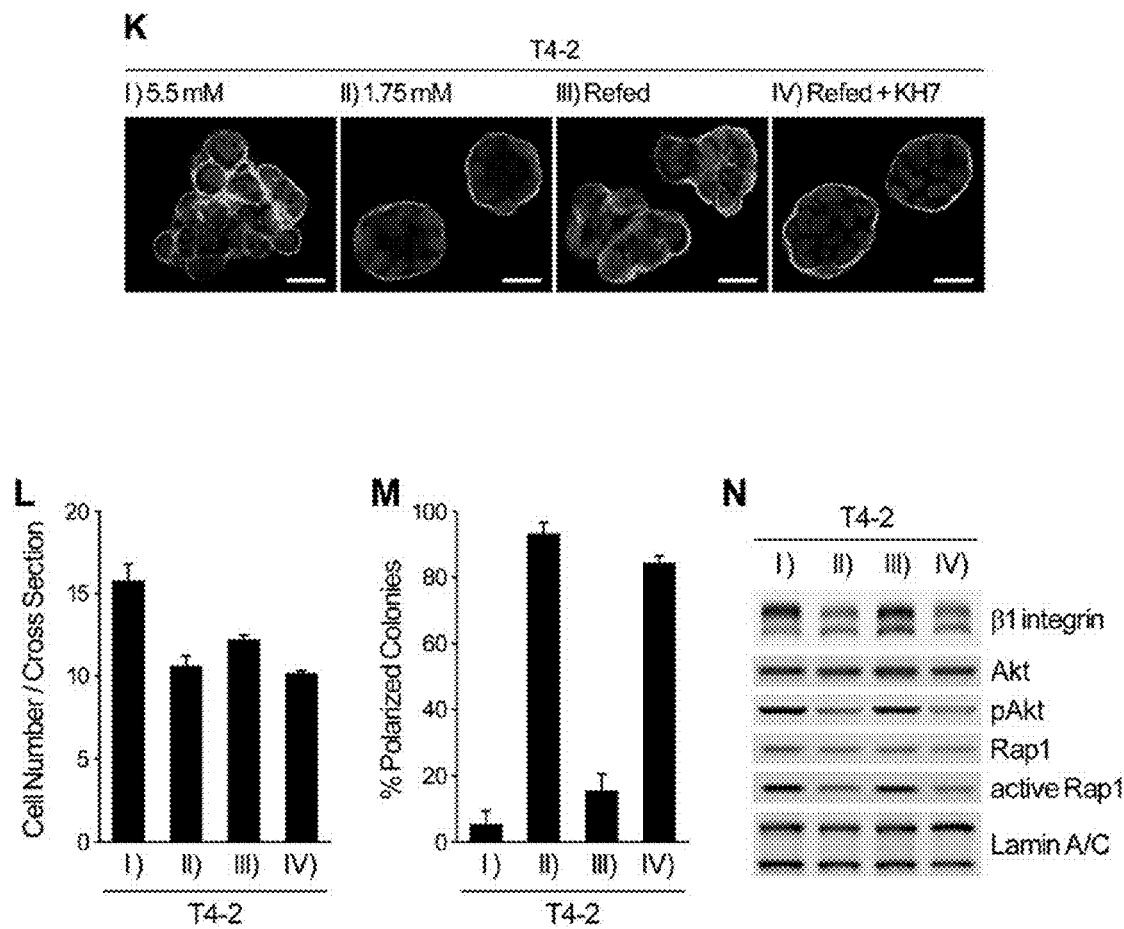

FIG. 8F shows confocal IF images of T4-2 cells cultured in 3D lrECM with low glucose (1.75 mM) or IA (20 μM), with or without 8CPT-2"-OMe-cAMP (ESCA, 20 μM Stained are α6 integrin and nuclei, shown as lighter in contrast. Bars, 20 μm. FIGS. 8G and 8H show cell numbers at the colony mid-section (FIG. 8G) and percent colonies with basal polarity (FIG. 8H) in conditions shown in FIG. 8F. FIG. 8I shows protein expression and/or activation of β1 integrin, Akt and Rap1 in conditions shown in FIG. 8F. FIG. 8J shows a scheme of reactivation of T4-2 cells reverted by 1.75 mM glucose to examine the effect of KH7. FIG. 8K shows confocal IF images of T4-2 cells cultured in conditions indicated in FIG. 8J. Stained are α6 integrin and nuclei, shown as lighter in contrast. Bars, 20 μm. FIGS. 8L and 8M show cell numbers at the colony mid-section (FIG. 8L) and percent colonies with basal polarity (FIG. 8M) in conditions indicated in FIG. 8J. FIG. 8N shows protein expression and/or activation of β1 integrin, Akt and Rap1 in conditions indicated in FIG. 8J.

Furthermore, supplementation of 8CPT-2'-OMe-cAMP, an EPAC-selective cAMP analogue (ESCA, Enserink et al., 2002), to T4-2 cells treated with IA or cultured with 1.75 mM glucose reactivated Rap1 and partially restored β1 integrin level and Akt activation leading to loss of tissue polarity (FIGS. 8F-8I). Notably treatment with ESCA did not restore proliferation to the level of non-treated cultures (FIG. 8G) suggesting that the glycolytic pathway is still required for maximum proliferation capacity.

Rap1 Activation in Response to Glycolysis Requires cAMP Production Via Soluble Adenylyl Cyclase The above data indicated that cAMP, the endogenous EPAC activator, also may be regulated by changes in glucose metabolism. T4-2 cells were reverted to form acinus-like structures by culturing in 1.75 mM glucose and then allowed to disorganize again by increasing glucose concentration to 5.5 mM which in turn reactivated expression of Rap1, β1 integrin and Akt (FIGS. 8J-8N). However, reactivation was almost completely abolished by treatment with KH7 (FIGS. 8K-8N), a specific inhibitor of the soluble adenylyl cyclase (sAC) that catalyzes the conversion of ATP to cAMP and is known to be involved in glucose-induced cAMP production in pancreatic β cells (Kamenetsky et al., 2006; Ramos et al., 2008). Consistently we showed that siRNA knockdown of sAC induced phenotypic reversion in T4-2 cells (FIGS. 9A-9D). Collectively these results suggest that sAC is responsible for glycolysis-mediated cAMP regulation, which in turn activates EPAC-Rap1 pathway.

Figures 9A, 9B, 9C, 9D:
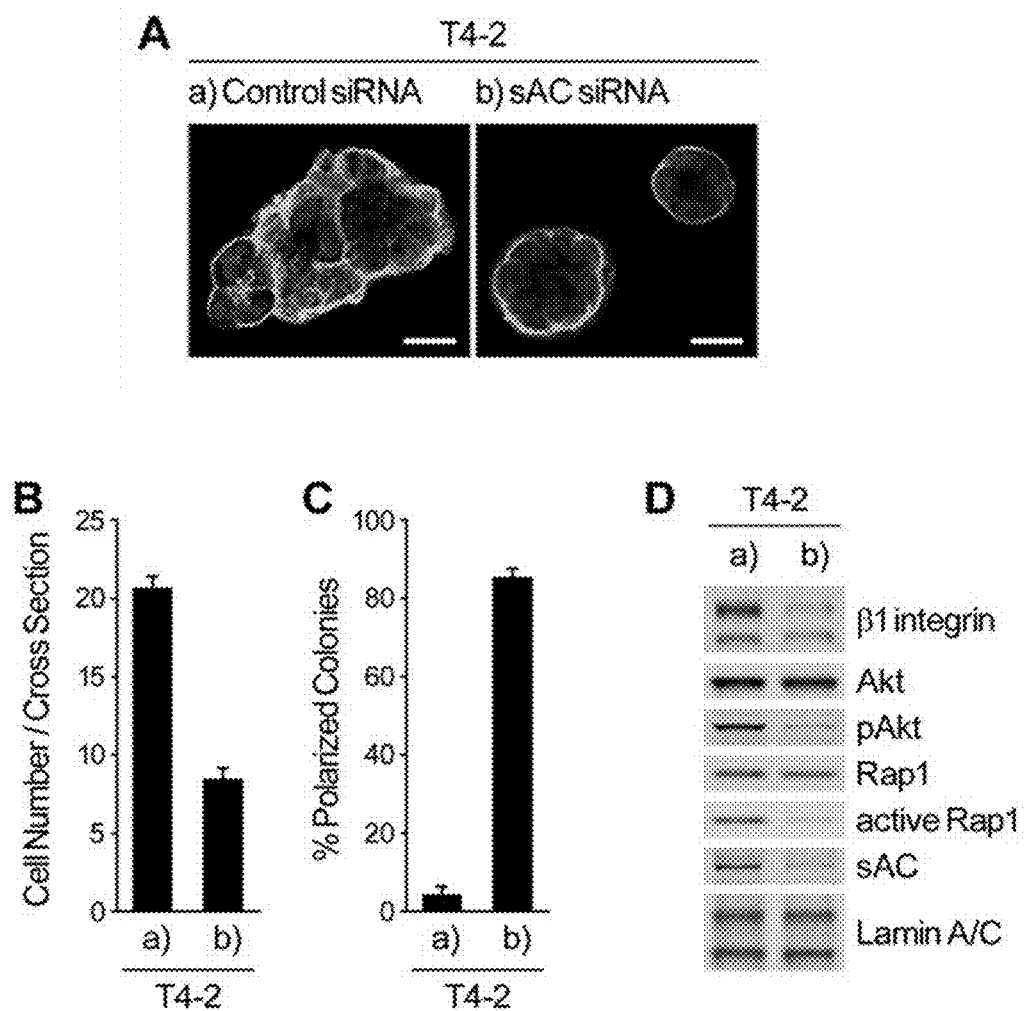
FIG. 9A, 9B, 9C, 9D is a series of images and graphs showing that knockdown of sAC suppresses Rap1 activity and malignant phenotype.

Additionally, FIG. 9A shows confocal IF images of T4-2 cells transfected with control or sAC siRNA, cultured in 3D-OT lrECM. α6 integrin, nuclei. Bars, 20 μm. FIGS. 9B and 9C show cell numbers at the colony mid-section (FIG. 9B) and percent colonies with basal polarity (FIG. 9C) in conditions shown in FIG. 9A. FIG. 9D shows Western blots of signaling intermediates in conditions shown in FIG. 9A.

Figures 10A, 10B, 10C:
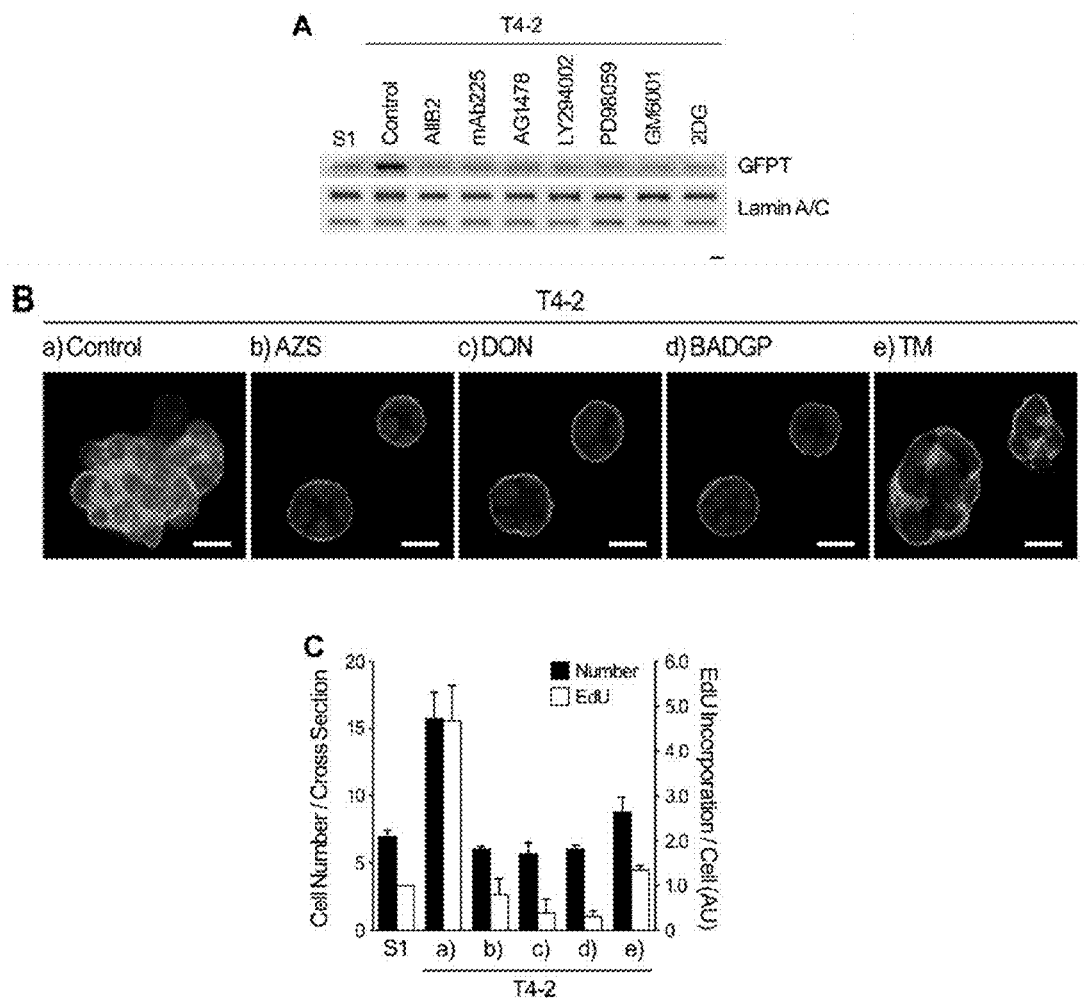
FIG. 10A, 10B, 10C, and FIG. 10D, 10E, 10F, 10G, 10H, 10I is a series of images and graphs showing that the hexosamine biosynthetic pathway supports oncogenic signaling and malignant phenotype through O-GlcNAcylation.
Figures 10D, 10E, 10F, 10G, 10H, 10I:
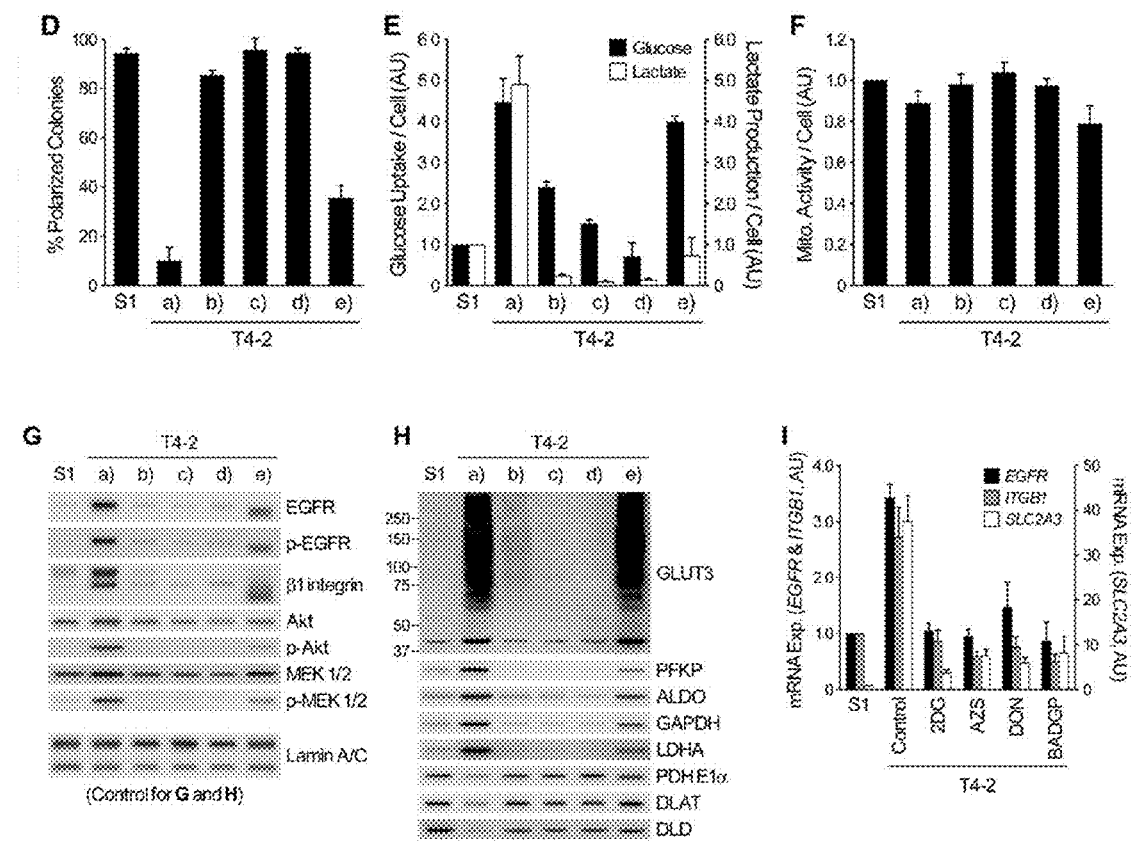

Hexosamine Biosynthetic Pathway (HBP) Regulates Key Signaling Pathways in Malignant Phenotype Through O-Linked N-Acetylglucosamine Modification The fact that the EGFR and MEK were not affected appreciably when only a portion of glycolytic pathway was inhibited by IA or OX (FIG. 5A-5J) led us to explore what other aspects of increased glucose metabolism were involved in their regulation. The microarray data of S1, T4-2 and reverted T4-2 cells suggested that the level of glutamine: fructose-6-phosphate transaminase (GFPT), the first and rate-limiting enzyme of HBP, was high in T4-2 cells (data not shown). HBP has been dubbed a "glucose sensing pathway" (Marshall, 2006; see also FIG. 1) and indeed, western blots showed that the expression of GFPT protein was higher in T4-2 cells compared to S1 and reverted T4-2 cells (FIG. 10A). Two different inhibitors of GFPT, azaserine (AZS) and 6-diazo-5-oxonorleucine (DON) induced the repertoire of the reversion phenotype: growth arrest, re-establishment of tissue polarity, suppression of activation of oncogenic signaling and reduction of glycolytic activity (FIGS. 10B-10H). Under these conditions, EGFR expression and activity were significantly down-regulated as were glucose uptake and lactate production, whereas as expected, mitochondrial activity remained unaltered (FIGS. 10E-10G).

FIG. 10A shows a Western blot of GFPT in S1, T4-2 and T4-2 cells reverted with 2DG or different signaling inhibitors (see FIG. 1A). Note that lamin A/C is a control blot for both FIGS. 10A and 3A. FIG. 10B shows a confocal IF images of T4-2 cells cultured in 3D lrECM with or without inhibitors of GFPT (azaserine [Azs, 20 μM] or 6-diazo-5-oxonorleucine [DON, 20 μM]), O-GlcNAc transferase (benzyl-2-acetamido-2-deoxy-α-D-galactopyranoside [BADGP, 5 mM]) or N-glycosylation (tunicamycin [TM, 10 ng/ml]). α6 integrin, nuclei. Bars, 20 μm. FIGS. 10C-10F show cell numbers at the colony mid-section (black bars, FIG. 10C), EdU incorporation per cells (white bars, FIG. 10C), percent colonies with basal polarity (FIG. 10D), glucose uptake (black bars, FIG. 10E), lactate production (white bars, FIG. 10E) and mitochondrial oxidation (FIG. 10F) in conditions shown in FIG. 10B. FIGS. 10G and 10H show Western blots of signaling intermediates (FIG. 10G) and GLUT3 and metabolic enzymes (FIG. 10H) in conditions shown in FIG. 10B. Note that the lamin A/C is a control for both FIG. 10G and FIG. 10H. FIG. 10I shows mRNA expression of EGFR, ITGB1 ($\beta$1 integrin) and GLUT3 (GLUT3) in S1, T4-2 and T4-2 cells reverted by metabolic inhibitors. Expression level of each gene was normalized with respect to 18S ribosomal RNA levels.

Figures 11A, 11B, 11C, 11D:
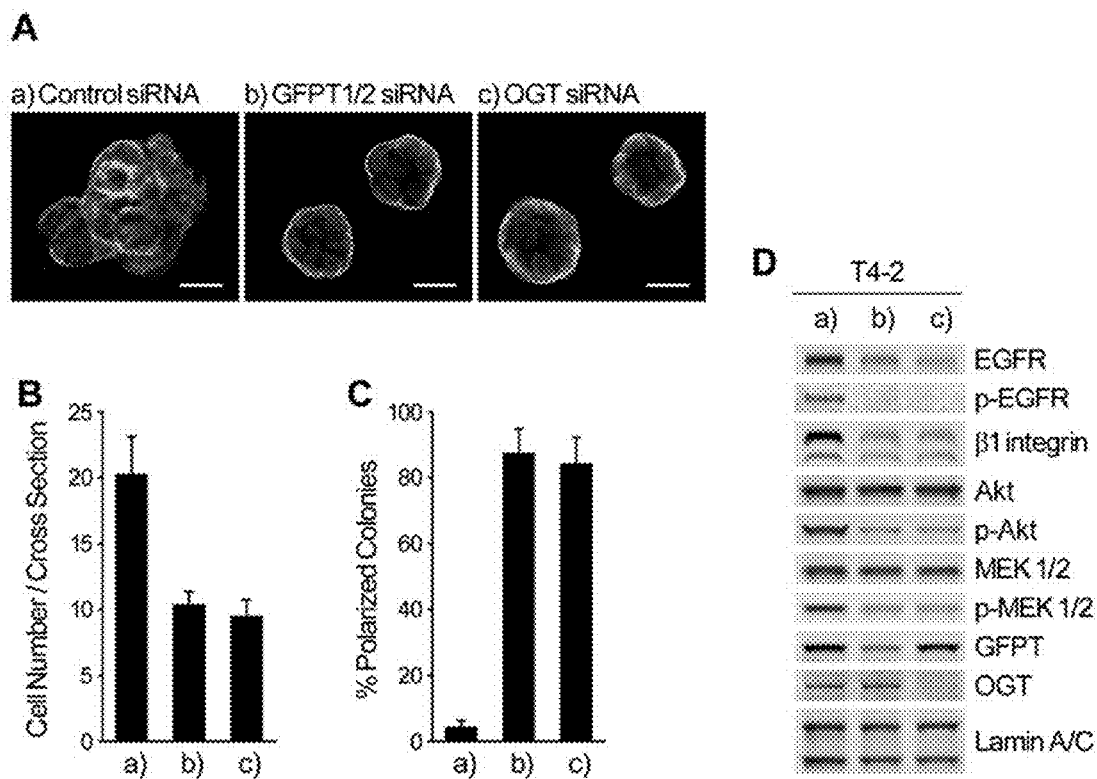
FIG. 11A, 11B, 11C, 11D is a series of images and bar graphs showing that knockdown of GFPT or OGT induce phenotypic reversion.

HBP branches into N-linked glycosylation and O-linked N-acetylglucosamine (O-GlcNAc) modification (see FIG. 1). Benzyl-2-acetamido-2-deoxy-$\alpha$-D-galactopyranoside (BADGP), which inhibits O-GlcNAc tranferase (OGT)-mediated O-GlcNAc modification on some proteins (Park et al., 2007), also induced phenotypic reversion (FIGS. 10B-10H). These results were essentially reproduced by knockdown of GFPT1/2 or OGT by siRNA in T4-2 cells (FIGS. 11A-11D). FIG. 11A shows confocal IF images of T4-2 cells transfected with control, GFPT1/2 or OGT siRNA, cultured in 3D-OT lrECM. $\alpha$6 integrin, nuclei. Bars, 20 $\mu$m. FIGS. 11B and 11C show cell numbers at the colony mid-section (FIG. 11B) and percent colonies with basal polarity (FIG. 11C) in conditions shown in FIG. 11A. FIG. 11D shows Western blots of signaling intermediates in conditions shown in FIG. 11A.

Since O-GlcNAc modification is known to be involved in many transcriptional events (Issad and Kuo, 2008), we examined mRNA levels of EGFR, $\beta$1 integrin and GLUT3. Treatment with the above inhibitors as well as 2DG, effectively suppressed their mRNA expression (FIG. 10I). In contrast, inhibition of N-linked glycosylation by tunicamycin (TM) did not lead to phenotypic reversion (FIGS. 10B-10H; and FIG. 1) despite the fact that increasing amounts of tunicamycin induced significant cell death (data not shown). These data indicate that O-GlcNAc modification downstream of HBP has a fundamental role in transcriptional regulation of EGFR, $\beta$1 integrin and GLUT3.

Application to Other Breast Cancer Cells and to Patient Data:

To show the generality of the above findings, we examined two additional human breast cell lines which display different phenotypes in 3D lrECM: HCC70 and MDA-MB-231 (Kenny et al., 2007). When HCC70 were deprived of glucose or treated with IA or DON, the reversion phenotype was similar to that in T4-2 cells (FIGS. 12A-12D). In the metastatic MDA-MB-231 cells, the altered phenotype was incomplete but still significant: There was appreciable decrease in proliferation, invasive property and other signaling activities (FIGS. 12E-12H).

Figures 12A, 12B, 12C, 12D:
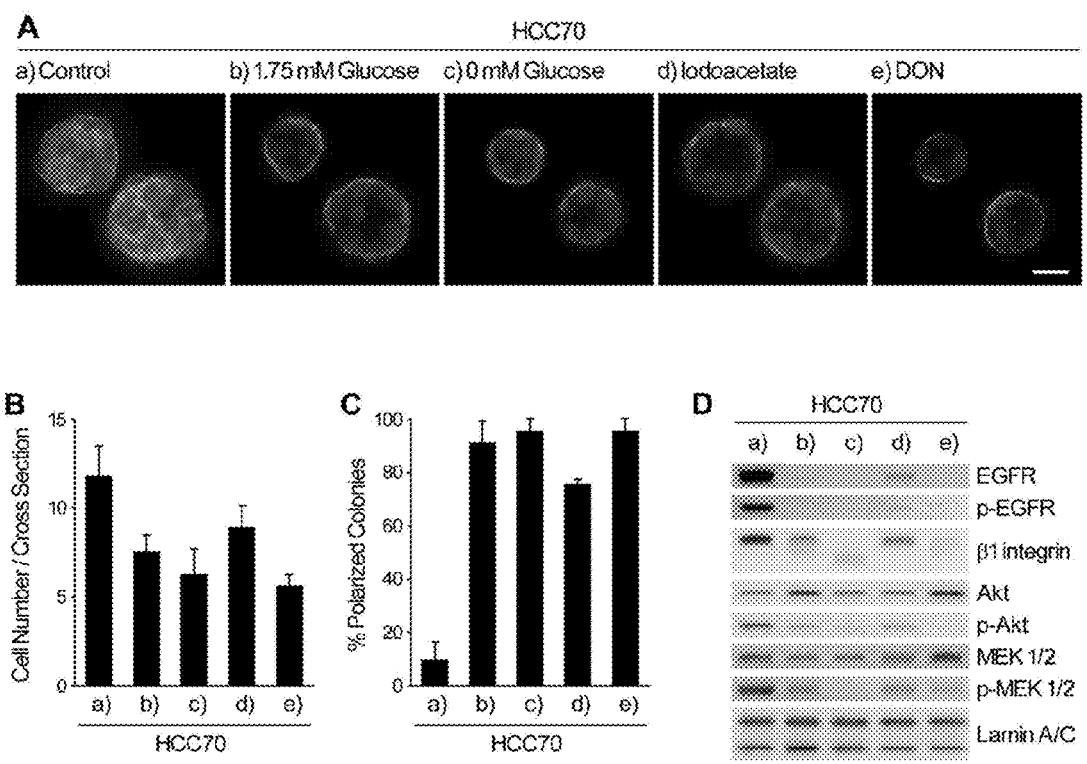
FIG. 12A, 12B, 12C, 12D and FIG. 12E, 12F, 12G, 12H is a series of images and bar graphs showing that other breast cancer cell lines also exhibit suppression of malignant phenotype when glucose uptake and metabolism are inhibited.
Figures 12E, 12F, 12G, 12H:
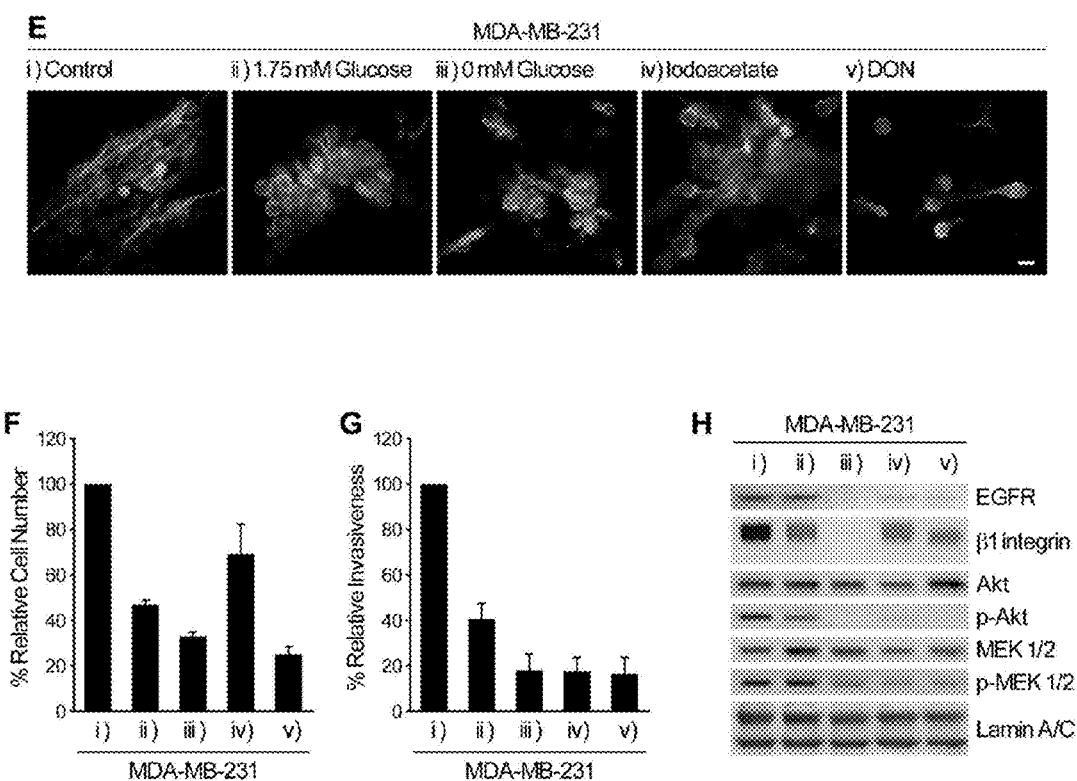

FIG. 12A shows confocal IF images of HCC70 cells cultured in 3D lrECM with 0 or 1.75 mM glucose, IA (2 $\mu$M) or DON (20 $\mu$M). $\alpha$6 integrin, nuclei. Bars, 20 $\mu$m. FIGS. 12B and 12C show cell numbers at the colony mid-section (FIG. 12B) and percent colonies with basal polarity (FIG. 12C) in conditions shown in FIG. 12A. FIG. 12D shows Western blots of signaling intermediates in conditions shown in FIG. 12A. FIG. 12E shows confocal IF images of MDA-MB-231 metastatic cells cultured in 3D with 0-1.75 mM glucose, IA (40 $\mu$M) or DON (20 $\mu$M). Phalloidin-staining of $\beta$-actin, nuclei. Bars, 20 $\mu$m. FIGS. 12F and 12G show total cell numbers (FIG. 12F) and invasive activity (FIG. 12G) in cells from FIG. 12E. FIG. 12H shows Western blots of signaling intermediates in conditions shown in FIG. 12E.

Figures 13A, 13B, 13C, 13D, 13E, 13F:
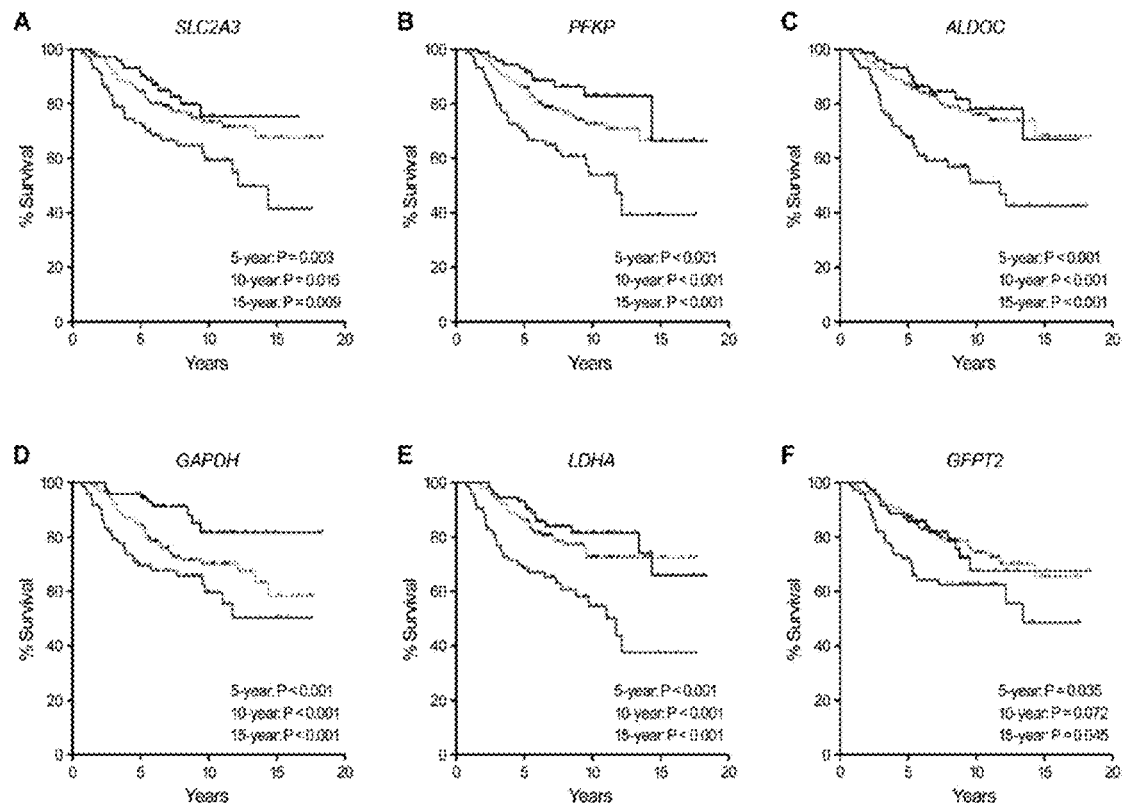
FIG. 13A, 13B, 13C, 13D, 13E, 13F is a series of graphs showing Kaplan-Meier survival analysis of prior art microarray dataset of samples from 295 breast cancer patients.

The literature linking increased glucose metabolism with poor patient outcome has been receiving increasing attention (Deshpande et al., 1981; Larson, 2004). We examined the published Agilent microarray dataset of 295 breast cancer patients (van de Vijver et al., 2002) and found significant correlation between poor prognosis and higher expression of glycolytic enzymes (PFKP, ALDOC, GAPDH, LDHA) or GLUT3 (FIGS. 13A-13E). P values represent the log-rank comparison between the upper and lower quartiles of marker expression evaluated at 5, 10 and 15 years after surgery. Statistical analysis showed that higher expression of GFPT2 also correlated with poor prognosis (FIG. 13F).

REFERENCES

1. Barcellos-Hoff, M. H., Aggeler, J., Ram, T. G., and Bissell, M. J. (1989). Functional differentiation and alveolar morphogenesis of primary mammary cultures on reconstituted basement membrane. Development 105, 223-235.
2. Beliveau, A., Mott, J. D., Lo, A., Chen, E. I., Koller, A. A., Yaswen, P., Muschler, J., and Bissell, M. J. (2010). Raf-induced MMP9 disrupts tissue architecture of human breast cells in three-dimensional culture and is necessary for tumor growth in vivo. Genes Dev 24, 2800-2811.
3. Bensaad, K., Tsuruta, A., Selak, M. A., Vidal, M. N., Nakano, K., Bartrons, R., Gottlieb, E., and Vousden, K. H. (2006). TIGAR, a p53-inducible regulator of glycolysis and apoptosis. Cell 126, 107-120.
4. Bissell, M. J. (1981). The differentiated state of normal and malignant cells or how to define a "normal" cell in culture. Int Rev Cytol 70, 27-100.
5. Bissell, M. J., Kenny, P. A., and Radisky, D. C. (2005). Microenvironmental regulators of tissue structure and function also regulate tumor induction and progression: the role of extracellular matrix and its degrading enzymes. Cold Spring Harb Symp Quant Biol 70, 343-356.
6. Bissell, M. J., Rambeck, W. A., White, R. C., and Bassham, J. A. (1976). Glycerol phosphate shuttle in virus-transformed cells in culture. Science 191, 856-858.
7. Briand, P., Petersen, O. W., and Van Deurs, B. (1987). A new diploid nontumorigenic human breast epithelial cell line isolated and propagated in chemically defined medium. In Vitro Cell Dev Biol 23, 181-188.
8. Chen, Z., Lu, W., Garcia-Prieto, C., and Huang, P. (2007). The Warburg effect and its cancer therapeutic implications. J Bioenerg Biomembr 39, 267-274.
9. Deshpande, N., Mitchell, I., and Millis, R. (1981). Tumour enzymes and prognosis in human breast cancer. Eur J Cancer 17, 443-448.
10. Dupuy, A. G., L'Hoste, S., Cherfils, J., Camonis, J., Gaudriault, G., and de Gunzburg, J. (2005). Novel Rap1 dominant-negative mutants interfere selectively with C3G and Epac. Oncogene 24, 4509-4520.
11. Enserink, J. M., Christensen, A. E., de Rooij, J., van Triest, M., Schwede, F., Genieser, H. G., Doskeland, S. O., Blank, J. L., and Bos, J. L. (2002). A novel Epac-specific cAMP analogue demonstrates independent regulation of Rap1 and ERK. Nat Cell Biol 4, 901-906.
12. Fournier, M. V., Martin, K. J., Kenny, P. A., Xhaja, K., Bosch, I., Yaswen, P., and Bissell, M. J. (2006). Gene expression signature in organized and growth-arrested mammary acini predicts good outcome in breast cancer. Cancer Res 66, 7095-7102.
13. Frezza, C., and Gottlieb, E. (2009). Mitochondria in cancer: not just innocent bystanders. Semin Cancer Biol 19, 4-11.

14. Gatenby, R. A., and Gillies, R. J. (2004). Why do cancers have high aerobic glycolysis? Nat Rev Cancer 4, 891-899.
15. Giovannucci, E., Harlan, D. M., Archer, M. C., Bergenstal, R. M., Gapstur, S. M., Habel, L. A., Pollak, M., Regensteiner, J. G., and Yee, D. (2010). Diabetes and cancer: a consensus report. CA Cancer J Clin 60, 207-221.
16. Godoy, A., Ulloa, V., Rodriguez, F., Reinicke, K., Yanez, A. J., Garcia Mde, L., Medina, R. A., Carrasco, M., Barberis, S., Castro, T., et al. (2006). Differential subcellular distribution of glucose transporters GLUT1-6 and GLUT9 in human cancer: ultrastructural localization of GLUT1 and GLUT5 in breast tumor tissues. J Cell Physiol 207, 614-627.
17. Hart, G. W., Housley, M. P., and Slawson, C. (2007). Cycling of O-linked beta-N-acetylglucosamine on nucleocytoplasmic proteins. Nature 446, 1017-1022.
18. Hjartaker, A., Langseth, H., and Weiderpass, E. (2008). Obesity and diabetes epidemics: cancer repercussions. Adv Exp Med Biol 630, 72-93.
19. Issad, T., and Kuo, M. (2008). O-GlcNAc modification of transcription factors, glucose sensing and glucotoxicity. Trends Endocrinol Metab 19, 380-389.
20. Itoh, M., Nelson, C. M., Myers, C. A., and Bissell, M. J. (2007). Rap1 integrates tissue polarity, lumen formation, and tumorigenic potential in human breast epithelial cells. Cancer Res 67, 4759-4766.
21. James, L. R., Ingram, A., Ly, H., That, K., Cai, L., and Scholey, J. W. (2001). Angiotensin II activates the GFAT promoter in mesangial cells. Am J Physiol Renal Physiol 281, F151-162.
22. Kamenetsky, M., Middelhaufe, S., Bank, E. M., Levin, L. R., Buck, J., and Steegborn, C. (2006). Molecular details of cAMP generation in mammalian cells: a tale of two systems. J Mol Biol 362, 623-639.
23. Kenny, P. A., and Bissell, M. J. (2007). Targeting TACE-dependent EGFR ligand shedding in breast cancer. J Clin Invest 117, 337-345.
24. Kenny, P. A., Lee, G. Y., Myers, C. A., Neve, R. M., Semeiks, J. R., Spellman, P. T., Lorenz, K., Lee, E. H., Barcellos-Hoff, M. H., Petersen, O. W., et al. (2007). The morphologies of breast cancer cell lines in three-dimensional assays correlate with their profiles of gene expression. Mol Oncol 1, 84-96.
25. Kroemer, G., and Pouyssegur, J. (2008). Tumor cell metabolism: cancer's Achilles' heel. Cancer Cell 13, 472-482.
26. Larson, S. M. (2004). Positron emission tomography-based molecular imaging in human cancer: exploring the link between hypoxia and accelerated glucose metabolism. Clin Cancer Res 10, 2203-2204.
27. Levine, A. J., and Puzio-Kuter, A. M. (2010). The control of the metabolic switch in cancers by oncogenes and tumor suppressor genes. Science 330, 1340-1344.
28. Litvin, T. N., Kamenetsky, M., Zarifyan, A., Buck, J., and Levin, L. R. (2003). Kinetic properties of "soluble" adenylyl cyclase. Synergism between calcium and bicarbonate. J Biol Chem 278, 15922-15926.
29. Liu, H., Radisky, D. C., Wang, F., and Bissell, M. J. (2004). Polarity and proliferation are controlled by distinct signaling pathways downstream of PI3-kinase in breast epithelial tumor cells. J Cell Biol 164, 603-612.
30. Marshall, S. (2006). Role of insulin, adipocyte hormones, and nutrient-sensing pathways in regulating fuel metabolism and energy homeostasis: a nutritional perspective of diabetes, obesity, and cancer. Sci STKE 2006, re1.
31. Marty, N., Dallaporta, M., and Thorens, B. (2007). Brain glucose sensing, counterregulation, and energy homeostasis. Physiol (Bethesda) 22, 241-251.
32. McKnight, S. L. (2010). On getting there from here. Science 330, 1338-1339.
33. Morici, G., Agnello, M., Spagnolo, F., Roccheri, M. C., Di Liegro, C. M., and Rinaldi, A. M. (2007). Confocal microscopy study of the distribution, content and activity of mitochondria during Paracentrotus lividus development. J Microsc 228, 165-173.
34. Muthuswamy, S. K., Li, D., Lelievre, S., Bissell, M. J., and Brugge, J. S. (2001). ErbB2, but not ErbB1, reinitiates proliferation and induces luminal repopulation in epithelial acini. Nat Cell Biol 3, 785-792.
35. Park, C. C., Zhang, H. J., Yao, E. S., Park, C. J., and Bissell, M. J. (2008). Beta1 integrin inhibition dramatically enhances radiotherapy efficacy in human breast cancer xenografts. Cancer Res 68, 4398-4405.
36. Park, J., Kwon, H., Kang, Y., and Kim, Y. (2007). Proteomic analysis of O-GlcNAc modifications derived from streptozotocin and glucosamine induced beta-cell apoptosis. J Biochem Mol Biol 40, 1058-1068.
37. Paterson, A. J., and Kudlow, J. E. (1995). Regulation of glutamine:fructose-6-phosphate amidotransferase gene transcription by epidermal growth factor and glucose. Endocrinology 136, 2809-2816.
38. Petersen, O. W., Ronnov-Jessen, L., Howlett, A. R., and Bissell, M. J. (1992). Interaction with basement membrane serves to rapidly distinguish growth and differentiation pattern of normal and malignant human breast epithelial cells. Proc Natl Acad Sci USA 89, 9064-9068.
39. Ramos, L. S., Zippin, J. H., Kamenetsky, M., Buck, J., and Levin, L. R. (2008). Glucose and GLP-1 stimulate cAMP production via distinct adenylyl cyclases in INS-1E insulinoma cells. J Gen Physiol 132, 329-338.
40. Rizki, A., Weaver, V. M., Lee, S. Y., Rozenberg, G. I., Chin, K., Myers, C. A., Bascom, J. L., Mott, J. D., Semeiks, J. R., Grate, L. R., et al. (2008). A human breast cell model of preinvasive to invasive transition. Cancer Res 68, 1378-1387.
41. Schuit, F. C., Huypens, P., Heimberg, H., and Pipeleers, D. G. (2001). Glucose sensing in pancreatic beta-cells: a model for the study of other glucose-regulated cells in gut, pancreas, and hypothalamus. Diabetes 50, 1-11.
42. Severson, E. A., Lee, W. Y., Capaldo, C. T., Nusrat, A., and Parkos, C. A. (2009). Junctional adhesion molecule A interacts with Afadin and PDZ-GEF2 to activate Rap1A, regulate beta1 integrin levels, and enhance cell migration. Mol Biol Cell 20, 1916-1925.
43. Shackelford, D. B., and Shaw, R. J. (2009). The LKB1-AMPK pathway: metabolism and growth control in tumour suppression. Nat Rev Cancer 9, 563-575.
44. van de Vijver, M. J., He, Y. D., van't Veer, L. J., Dai, H., Hart, A. A., Voskuil, D. W., Schreiber, G. J., Peterse, J. L., Roberts, C., Marton, M. J., et al. (2002). A gene-expression signature as a predictor of survival in breast cancer. N Engl J Med 347, 1999-2009.
45. Vander Heiden, M. G., Cantley, L. C., and Thompson, C. B. (2009). Understanding the Warburg effect: the metabolic requirements of cell proliferation. Science 324, 1029-1033.
46. Vaughn, A. E., and Deshmukh, M. (2008). Glucose metabolism inhibits apoptosis in neurons and cancer cells by redox inactivation of cytochrome c. Nat Cell Biol 10, 1477-1483.
47. Wang, F., Hansen, R. K., Radisky, D., Yoneda, T., Barcellos-Hoff, M. H., Petersen, O. W., Turley, E. A., and Bissell, M. J. (2002). Phenotypic reversion or death of cancer cells by altering signaling pathways in three-dimensional contexts. J Natl Cancer Inst 94, 1494-1503.
48. Wang, F., Weaver, V. M., Petersen, O. W., Larabell, C. A., Dedhar, S., Briand, P., Lupu, R., and Bissell, M. J. (1998). Reciprocal interactions between beta1-integrin and epidermal growth factor receptor in three-dimensional basement membrane breast cultures: a different perspective in epithelial biology. Proc Natl Acad Sci USA 95, 14821-14826.
49. Warburg, O. (1956). On the origin of cancer cells. Science 123, 309-314.
50. Weaver, V. M., Lelievre, S., Lakins, J. N., Chrenek, M. A., Jones, J. C., Giancotti, F., Werb, Z., and Bissell, M. J. (2002). beta4 integrin-dependent formation of polarized three-dimensional architecture confers resistance to apoptosis in normal and malignant mammary epithelium. Cancer Cell 2, 205-216.
51. Weaver, V. M., Petersen, O. W., Wang, F., Larabell, C. A., Briand, P., Damsky, C., and Bissell, M. J. (1997). Reversion of the malignant phenotype of human breast cells in three-dimensional culture and in vivo by integrin blocking antibodies. J Cell Biol 137, 231-245.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A method, comprising:

measuring an expression level of at least one cellular marker selected from the group consisting of: platelet-type phosphofructokinase (PFKP); glyceraldehyde-3-phosphate dehydrogenase (GAPDH); aldolase (ALDO); lactate dehydrogenase A (LDHA); glucose transporter 3 (GLUT3); and glutamine-fructose-6-phosphate transaminase (GFPT), in a cell suspected of having increased oncogenic signaling; and determining whether the measured expression level of said at least one cellular marker in said cell suspected of having increased oncogenic signaling is increased relative to the expression level of said at least one cellular marker in a reference cell.

2. The method of claim 1 further comprising measuring the expression level of at least one of epidermal growth factor receptor (EGFR) and integrin beta 1 (ITGB1).

3. The method of claim 1 wherein said measuring an expression level consists of measuring the expression level of PFKP, GAPDH, ALDO and LDHA.

4. The method of claim 1 wherein said measuring consists of measuring a level of GLUT3.

5. The method of claim 1 wherein said measuring an expression level comprises the step of measuring the expression of mRNA encoding protein corresponding to a marker.

6. The method of claim 1 wherein said expression level is determined by use of a microarray containing nucleic acids hybridizing to a cellular marker being measured.

7. The method of claim 1 wherein said expression level is measured by a method selected from the group consisting of Northern blotting, serial analysis of gene expression (SAGE), and reverse transcription polymerase chain reaction (rt-PCR).

8. The method of claim 1 wherein said measuring an expression level comprises measuring a protein level.

9. The method of claim 8 wherein said measuring a protein level comprises contacting a cellular marker with an antibody specific for said cellular marker.

10. The method of claim 8 wherein said measuring is done by a method selected from the group consisting of ELISA and Western blot.

11. The method of claim 8 wherein said protein level is determined by isotope-coded affinity tags (ICAT).

12. The method of claim 1 wherein expression level of at least three markers is measured.

13. The method of claim 1 wherein said cell suspected of having increased oncogenic signaling is a human cell.

14. The method of claim 13 wherein said cell suspected of having increased oncogenic signaling is a breast epithelial cell.

15. The method of claim 14 wherein said cell suspected of having increased oncogenic signaling is a tumor cell.

* * * * *

SEQUENCE LISTING

```
<160> NUMBER OF SEQ ID NOS: 10

<210> SEQ ID NO 1
<211> LENGTH: 19
<212> TYPE: RNA
<213> ORGANISM: Artificial
<220> FEATURE:
<223> OTHER INFORMATION: GAPDH siRNA duplex sequence with dTdT attached
      to the 3' end

<400> SEQUENCE: 1
gagccacauc gcucagaca                                                    19

<210> SEQ ID NO 2
<211> LENGTH: 19
<212> TYPE: RNA
<213> ORGANISM: Artificial
<220> FEATURE:
<223> OTHER INFORMATION: GAPDH siRNA duplex sequence with dGdG attached
      to the 3' end

<400> SEQUENCE: 2
ugucugagcg auguggcuc                                                    19

<210> SEQ ID NO 3
<211> LENGTH: 19
<212> TYPE: RNA
<213> ORGANISM: Artificial
<220> FEATURE:
<223> OTHER INFORMATION: EPAC1 siRNA duplex sequence with dTdT attached
      to the 3' end

<400> SEQUENCE: 3
ccaucauccu gcgagaaga                                                    19

<210> SEQ ID NO 4
<211> LENGTH: 19
<212> TYPE: RNA
<213> ORGANISM: Artificial
<220> FEATURE:
<223> OTHER INFORMATION: EPAC1 siRNA duplex sequence with dTdG attached
      to the 3' end

<400> SEQUENCE: 4
ucuucucgca ggaugaugg                                                    19
```

<210> SEQ ID NO 5
<211> LENGTH: 19
<212> TYPE: RNA
<213> ORGANISM: Artificial
<220> FEATURE:
<223> OTHER INFORMATION: EPAC2 siRNA duplex sequence with dTdT attached
      to the 3' end

<400> SEQUENCE: 5
gaguuagcag guguucuca                                                    19

<210> SEQ ID NO 6
<211> LENGTH: 19
<212> TYPE: RNA
<213> ORGANISM: Artificial
<220> FEATURE:
<223> OTHER INFORMATION: EPAC2 siRNA duplex sequence with dTdC attached
      to the 3' end

<400> SEQUENCE: 6
ugagaacacc ugcuaacuc                                                    19

<210> SEQ ID NO 7
<211> LENGTH: 19
<212> TYPE: RNA
<213> ORGANISM: Artificial
<220> FEATURE:
<223> OTHER INFORMATION: sAC siRNA duplex sequence with dTdT attached to
      the 3' end

<400> SEQUENCE: 7
auguagccug gagauccau                                                    19

<210> SEQ ID NO 8
<211> LENGTH: 19
<212> TYPE: RNA
<213> ORGANISM: Artificial
<220> FEATURE:
<223> OTHER INFORMATION: sAC siRNA duplex sequence with dTdT attached to
      the 3' end

<400> SEQUENCE: 8
auggaucucc aggcuacau                                                    19

<210> SEQ ID NO 9
<211> LENGTH: 34
<212> TYPE: DNA
<213> ORGANISM: Artificial
<220> FEATURE:
<223> OTHER INFORMATION: GLUT3 PCR primer

<400> SEQUENCE: 9
cgggatccgc caccatgggg acacagaagg tcac                                   34

<210> SEQ ID NO 10
<211> LENGTH: 63
<212> TYPE: DNA
<213> ORGANISM: Artificial
<220> FEATURE:
<223> OTHER INFORMATION: GLUT3 PCR primer

<400> SEQUENCE: 10
aacccgggtc aagcataatc tggaacatcg tatggataga cattggtggt ggtctcctta       60
gca                                                                     63